US012692248B2

(12) United States Patent
Kaldor et al.

(10) Patent No.: US 12,692,248 B2
(45) Date of Patent: Jul. 28, 2026

(54) SOLID STATE FORMS OF (S)-N-(3-(2-(((R)-1-HYDROXYPROPAN-2-YL) AMINO)-6-MORPHOLINOPYRIDIN-4-YL)-4-METHYLPHENYL)-3-(2,2,2-TRIFLUOROETHYL)PYRROLIDINE-1-CARBOXAMIDE AND SALTS THEREOF

(71) Applicant: PIERRE FABRE MEDICAMENT, Lavaur (FR)

(72) Inventors: Stephen W. Kaldor, San Diego, CA (US); Toufike Kanouni, Palm Beach Gardens, FL (US); Andrew Phimister, Kensington, CA (US); Jayachandra P. Reddy, West Palm Beach, FL (US)

(73) Assignee: PIERRE FABRE MEDICAMENT, Lavaur (FR)

( * ) Notice: Subject to any disclaimer, the term of this patent is extended or adjusted under 35 U.S.C. 154(b) by 444 days.

(21) Appl. No.: 18/556,243

(22) PCT Filed: Apr. 21, 2022

(86) PCT No.: PCT/US2022/025815
§ 371 (c)(1),
(2) Date: Oct. 19, 2023

(87) PCT Pub. No.: WO2022/226221
PCT Pub. Date: Oct. 27, 2022

(65) Prior Publication Data

US 2024/0208931 A1 Jun. 27, 2024

Related U.S. Application Data

(60) Provisional application No. 63/178,752, filed on Apr. 23, 2021.

(51) Int. Cl.
*C07D 401/12* (2006.01)
*A61K 31/5377* (2006.01)

(52) U.S. Cl.
CPC ........ *C07D 401/12* (2013.01); *A61K 31/5377* (2013.01)

(58) Field of Classification Search
None
See application file for complete search history.

(56) References Cited

U.S. PATENT DOCUMENTS

| | | | |
|---|---|---|---|
| 5,846,514 | A | 12/1998 | Foster et al. |
| 6,334,997 | B1 | 1/2002 | Foster et al. |
| 10,927,111 | B2 | 2/2021 | Kaldaor et al. |
| 11,098,031 | B1 | 8/2021 | Kaldor et al. |
| 11,377,431 | B2 | 7/2022 | Kaldor et al. |
| 11,407,737 | B2 | 8/2022 | Kaldor et al. |
| 11,667,634 | B2 | 6/2023 | Kaldor et al. |
| 11,746,095 | B2 | 9/2023 | Kaldor et al. |
| 2004/0157827 | A1 | 8/2004 | Pevarello et al. |
| 2005/0256174 | A1 | 11/2005 | Wood et al. |
| 2007/0054916 | A1 | 3/2007 | Patel et al. |
| 2007/0244120 | A1 | 10/2007 | Dumas et al. |
| 2008/0114006 | A1 | 5/2008 | Flynn et al. |
| 2009/0036419 | A1 | 2/2009 | Chen et al. |
| 2009/0054436 | A1 | 2/2009 | Borzilleri et al. |
| 2011/0183997 | A1 | 7/2011 | Chianelli et al. |
| 2012/0040951 | A1 | 2/2012 | Chuaqui et al. |
| 2014/0275003 | A1 | 9/2014 | Barsanti et al. |
| 2015/0119392 | A1 | 4/2015 | Flynn et al. |
| 2016/0075727 | A1 | 3/2016 | Burger et al. |
| 2017/0260207 | A1 | 9/2017 | Aversa et al. |
| 2019/0175606 | A1 | 6/2019 | Aversa et al. |
| 2020/0347052 | A1 | 11/2020 | Kaldor et al. |
| 2021/0300904 | A1 | 9/2021 | Kaldor et al. |
| 2022/0340543 | A1 | 10/2022 | Kaldor et al. |
| 2023/0081390 | A1 | 3/2023 | Kaldaor et al. |
| 2023/0255977 | A1 | 8/2023 | Franovic et al. |

FOREIGN PATENT DOCUMENTS

| | | | |
|---|---|---|---|
| EP | 2112150 | B1 | 10/2013 |
| WO | WO-03068229 | A1 | 8/2003 |
| WO | WO-2006071940 | A2 | 7/2006 |
| WO | WO-2008034008 | A2 | 3/2008 |
| WO | WO-2013184119 | A1 | 12/2013 |
| WO | WO-2014151616 | A1 | 9/2014 |
| WO | WO-2016038581 | A1 | 3/2016 |
| WO | WO-2016038582 | A1 | 3/2016 |
| WO | WO 2020/024009 | A1 | 2/2020 |
| WO | WO-2020168172 | A1 | 8/2020 |
| WO | WO-2020198058 | A1 | 10/2020 |
| WO | WO-2020227020 | A1 | 11/2020 |
| WO | WO-2021081375 | A1 | 4/2021 |
| WO | WO-2022060996 | A1 | 3/2022 |
| WO | WO-2022081469 | A1 | 4/2022 |
| WO | WO-2022226221 | A1 | 10/2022 |
| WO | WO-2022226261 | A1 | 10/2022 |

OTHER PUBLICATIONS

Anastassiadis et al. Comprehensive assay of kinase catalytic activity reveals features of kinase inhibitor selectivity. Nat Biotechnol. 29(11):1039-45 (2011).
Berge et al. Pharmaceutical Salts. Journal of Pharmaceutical Sciences 66(1):1-19 (Jan. 1977).
CAS Chemical Structure Search #3191415 Updated (Apr. 2020).
CAS Chemical Structure Search dated Apr. 24, 2019.
CAS Search dated Apr. 26, 2023.
Chapman et al. Improved survival with vemurafenib in melanoma with BRAF V600E mutation. New England Journal of Medicine 364(26):2507-2516 (2011).
Chemical Structure Search report data Feb. 27, 2019.
Davies et al. Mutations of the BRAF Gene in Human Cancer. Nature 417:949-954 (2002).

(Continued)

*Primary Examiner* — Samantha L Shterengarts
(74) *Attorney, Agent, or Firm* — Birch, Stewart, Kolasch & Birch, LLP

(57) ABSTRACT

The present disclosure relates to solid state forms of (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide and salts thereof. Such solid state forms are useful in preparation of pharmaceutical compositions and dosage forms for the treatment of disease.

23 Claims, 14 Drawing Sheets

(56) References Cited

OTHER PUBLICATIONS

Evans. Synthesis of Radiolabelled Compounds. Journal of Radioanalytical Chemistry 64(1-2):9-32 (1981).
Hauschild et al. Dabrafenib in BRAF-mutated Metastatic Melanoma: A Multicentre, Open-Label, Phase 3 Randomised Controlled Trial. Lancet 380(9839):358-65 (2012).
Henry et al. Discovery of 1-(3,3-dimethylbutyl)-3-(2-fluoro-4-methyl-5-(7-methyl-2-(methylamino)pyrido[2,3-d]pyrimidin-6-yl)phenyl)urea (LY3009120) as a pan-RAF inhibitor with minimal paradoxical activation and activity against BRAF or RAS mutant tumor cells. J Med Chem 58:4165-4179 (2015).
Kabalka et al., The synthesis of radiolabeled compounds via organometallic intermediates. Tetrahedron 45(21):6601-6621 (1989).
Kania et al. The Discovery of Exarafenib (KIN-2787), a Solution to the Challenges of Pan-RAF kinase Inhibition. PowerPoint presentation at Winter Conference on Medicinal & Bioorganic Chemistry (Jan. 2023).
Kinnate Biopharma. RAF Clinico-Genomic Landscape Study PowerPoint. (Nov. 2021).
Lv et al. Design, synthesis and biological evaluation of novel 4-alkynylquinoline derivatives as PI3K/mTOR dual inhibitors. Eur J Med Chem 99:36-50 (2015).
Manabe. Antitumor activity of KIN-2787, a next-generation pan-RAF inhibitor, in preclinical models of human BRAF-alteration driven non-small cell lung cancer (NSCLC). Presentation from IASLC 2022 Targeted Therapies of Lung Cancer Meeting. Feb. 22-26, 2022.
Mckean et al. Design and rationale of a first in human (FIH) phase 1/1b study evaluating KIN-2787, a potent and highly selective pan-RAF inhibitor, in adult patients with BRAF- and NRAS-mutation positive solid tumors. American Association for Cancer Research Annual Meeting. Poster #CT248 (2022).
Miller et al. Antitumor activity of KIN-2787, a next-generation pan-RAF inhibitor, in preclinical models of human RAF/RAS mutant melanoma. American Association for Cancer Research Poster #2674 (2022).
Nishiguchi et al. Design and Discovery of N-(2-Methyl-5'-morpholino-6'-((tetrahydro-2H-pyran-4-yl)oxy)-[3,3'-bipyridin]-5-yl)-3-(trifluoromethyl)benzamide (RAF709): A Potent, Selective, and Efficacious RAF Inhibitor Targeting RAS Mutant Cancers. J Med Chem 60(12):4869-4881 (2017).
Owsley et al. Prevalence of class I-III BRAF mutations among 114,662 cancer patients in a large genomic database. Exp Biol Med (Maywood) 246(1):31-39 (2021).
PCT/US2020/024009 International Invitation to Pay Additional Fees dated Jun. 2, 2020.
PCT/US2020/024009 International Search Report and Written Opinion dated Jul. 28, 2020.
PCT/US2020/030786 International Invitation to Pay Additional Fees dated Jul. 14, 2020.
PCT/US2020/030786 International Search Report and Written Opinion dated Sep. 14, 2020.
PCT/US2020/057132 International Invitation to Pay Additional Fees dated Dec. 8, 2020.
PCT/US2020/057132 International Search Report and Written Opinion dated Feb. 9, 2021.
PCT/US2021/050690 International Search Report and Written Opinion dated Dec. 27, 2021.
PCT/US2021/054403 International Search Report and Written Opinion dated Dec. 28, 2021.
PCT/US2022/025815 International Search Report and Written Opinion dated Jul. 28, 2022.
PCT/US2022/025875 International Search Report and Written Opinion dated Jul. 25, 2022.
Ramurthy, Savithri, et al., Design and Discovery of N-(3-(2-(2-Hydroxyethoxy)-6-morpholinopyridin-4-yl)-4-methylphenyl)-2-(trifluoromethyl)isonicotinamide, a Selective, Efficacious, and Well-Tolerated RAF Inhibitor Targeting RAS Mutant Cancers: The Path to the Clinic. Journal of Medicinal Chemistry 63(5):2013-2027 (2020).
Reg/Caplus and Marpat. Science IP Report dated Sep. 17, 2020.
Rosse. Pyridyl Isonicotinamide Inhibitors of RAF Kinase. ACS Med. Chem. Lett. 7:1022-1023 (2016).
Science IP Report dated Jul. 13, 2020 (873 pgs).
Severson et al. Occurrence of BRAF class II and III alterations is common across solid tumors and is associated with inferior clinical outcomes in NSCLC and melanoma. American Association for Cancer Research Poster #4122 (2022).
Severson et al. Real-World Clinical Genomic Analysis of Patients with BRAF Mutated Cancers Identifies BRAF Class II and III as a Population of Unmet Medical Need. ESMO Targeted Anticancer Therapies Congress 2022. Poster 40P.
Spira et al. A Phase 1 Clinical Trial Evaluating Monotherapy With Exarafenib (KIN-2787), a Highly Selective Pan-RAF Inhibitor, in BRAF-Altered Solid Tumors and NRAS-Mutant Melanoma. PowerPoint Presentation American Association for Cancer Research Annual Meeting Apr. 14-19, 2023.
Subbiah et al. Pan-Cancer Efficacy of Vemurafenib in BRAF V600-Mutant Non-Melanoma Cancers. Cancer Discov 10(5):657-663 (2020).
U.S. Appl. No. 17/167,599 Office Action dated Oct. 31, 2022.
U.S. Appl. No. 17/738,327 Office Action dated Apr. 18, 2023.
U.S. Appl. No. 18/296,726 Office Action dated Jul. 18, 2023.
Wang et al. Exarafenib (KIN-2787) is a potent, selective pan-RAF inhibitor with activity in preclinical models of BRAF Class II/III mutant and NRAS mutant melanoma. American Association for Cancer Research Annual Meeting Poster #4927 (2023).
Yaeger et al. Targeting Alterations in the RAF-MEK Pathway. Cancer Discov 9(3):329-341 (2019).
Japanese Office Action for Japanese Application No. 2023-565206, dated Oct. 14, 2025, with partial English translation.

SOLID STATE FORMS OF (S)-N-(3-(2-(((R)-1-HYDROXYPROPAN-2-YL) AMINO)-6-MORPHOLINOPYRIDIN-4-YL)-4-METHYLPHENYL)-3-(2,2,2-TRIFLUOROETHYL) PYRROLIDINE-1-CARBOXAMIDE AND SALTS THEREOF

CROSS-REFERENCE TO RELATED APPLICATION

This application is a National Stage Entry of International Application No. PCT/US2022/025815, filed on Apr. 21, 2022, which claims the benefit of U.S. Provisional Patent Application No. 63/178,752, filed on Apr. 23, 2021, each of which is hereby incorporated by reference.

BACKGROUND OF THE INVENTION

RAF kinase functions in the Ras-Raf-MEK-ERK mitogen activated protein kinase (MAPK) pathway (also known as MAPK/ERK pathway) by phosphorylating and activating MEK. By altering the levels and activities of transcription factors, MAPK leads to altered transcription of genes that are important for the cell cycle. Deregulation of MAPK activity occurs frequently in tumors. Accordingly, therapies that target RAF kinase activity are desired for use in the treatment of cancer and other disorders characterized by aberrant MAPK/ERK pathway signaling. One such modulator of RAF kinase is (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide and pharmaceutically acceptable salts thereof.

SUMMARY OF THE INVENTION

The present disclosure relates to an amorphous solid state form of (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide, herein after known as Compound 1. The molecular structure of Compound 1 is shown below:

Compound 1

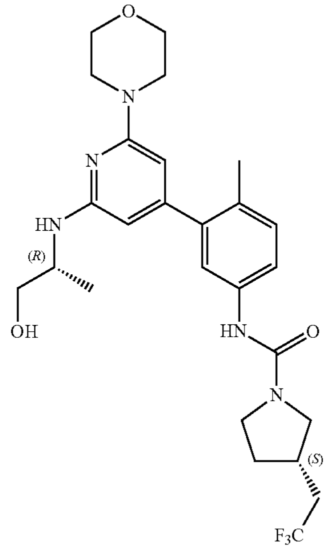

(S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide Also disclosed herein is a crystalline form of (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide hydrochloride, herein after known as Compound 2. The molecular structure of Compound 2 is shown below:

Compound 2

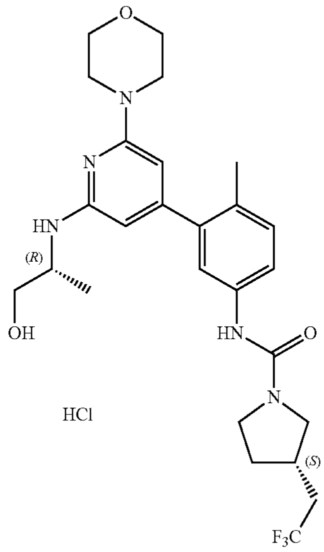

(S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide hydrochloride Also disclosed herein is a crystalline form of (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide hydrobromide, herein after known as Compound 3. The molecular structure of Compound 3 is shown below:

Compound 3

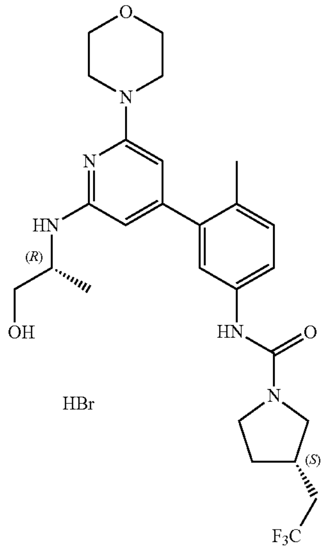

(S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide hydrobromide Also disclosed herein are crystalline forms I and II of (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide 4-methylbenzenesulfonate, herein after known as Compound 4. The molecular structure of Compound 4 is shown below:

Compound 4

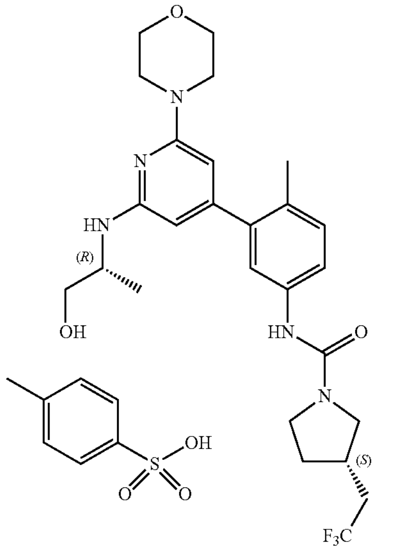

(S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide 4-methylbenzenesulfonate Also disclosed herein is a crystalline form of (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide phosphate, herein after known as Compound 5. The molecular structure of Compound 5 is shown below:

Compound 5

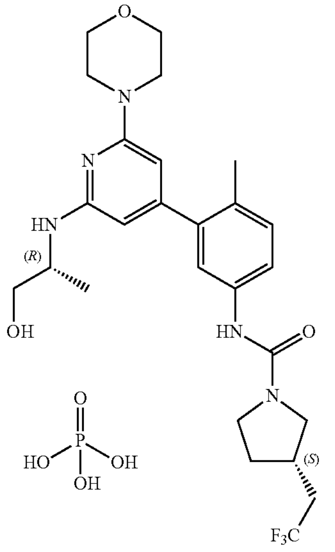

(S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide phosphate Also disclosed herein are crystalline forms I and II of (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide sulfate, herein after known as Compound 6. The molecular structure of Compound 6 is shown below:

Compound 6

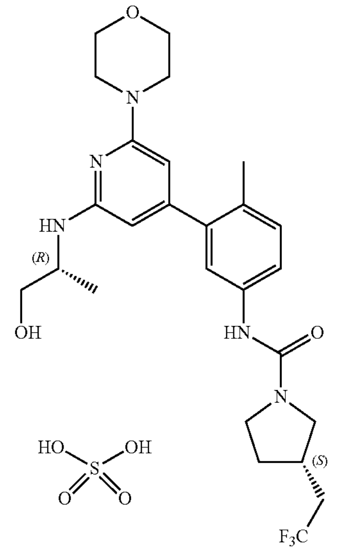

(S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide sulfate Provided herein are pharmaceutical compositions comprising solid state forms of Compound 1, Compound 2, Compound 3, Compound 4, Compound 5, Compound 6, or any combinations thereof, and a pharmaceutically acceptable excipient.

Also described herein is a method of inhibiting receptor tyrosine kinase effector RAF comprising administering to the subject with a condition in need thereof, the solid form of Compound 1, Compound 2, Compound 3, Compound 4, Compound 5, Compound 6, or any combinations thereof.

BRIEF DESCRIPTION OF THE DRAWINGS

The features of the invention are set forth with particularity in the appended claims. A better understanding of the features of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
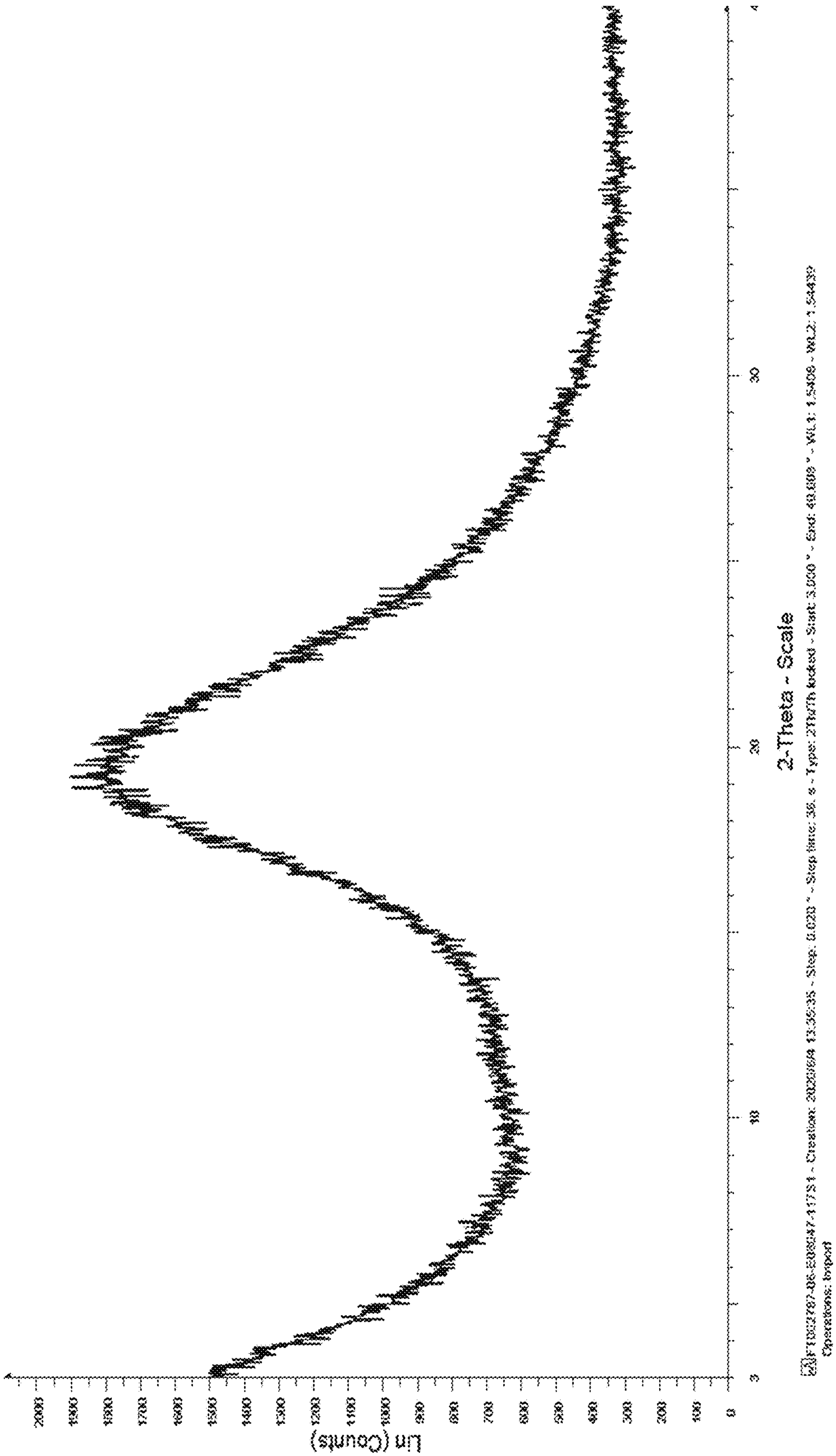
FIG. 1 shows an X-ray diffraction pattern of amorphous Compound 1.

Provided herein are compositions comprising solid state forms of Compound 1, Compound 2, Compound 3, Compound 4, Compound 5, Compound 6, or any combinations thereof.

In some embodiments, Compound 2 was found to have a number of unexpected advantages. Compound 2 is highly stable and identified as the thermodynamic product of all of the competitive slurry experiments conducted with amorphous Compound 2. Although Compound 2 is an anhydrate as identified by TGA, Compound 2 is minimally hygroscopic and has a high melting point, again demonstrating the compounds high stability. An additional benefit of Compound 2 is its increased solubility in aqueous media as compared to Compound 1.

Compound 3 was found to have similar endothermic data as compared to Compound 2.

Definitions

Unless defined otherwise, all technical and scientific terms used herein have the same meaning as is commonly understood by one of skill in the art to which this invention belongs.

All patents and publications referred to herein are incorporated by reference.

As used in the specification and claims, the singular form "a", "an" and "the" includes plural references unless the context clearly dictates otherwise.

The term "hydrate" and "solvate" are meant to describe crystalline Compound 1 forms that include an amount of water or solvent, as supported by data derived from differential scanning calorimetry (DSC) experiments, thermogravimetric analysis (TGA) experiments, X-ray diffraction experiments, and/or the procedure for generating the solid crystalline form. In some embodiments, a solvate crystalline form or hydrate crystalline form comprises at least 1.5%, 1.75%, 2.0%, 2.5%, 3.0%, 4.0%, 5.0%, 6.0%, 7.0%, 8.0%, 9.0%, 10.0%, 15.0%, or 20.0% of the total weight of the sample as water, solvent, or a combination thereof, as determined by TGA. In some embodiments, a solvate crystalline form or hydrate crystalline form exhibits at least one DSC endotherm onset before or within 30° C. of the boiling point of water or the solvent(s) used in the generation of the crystalline form. For example, a hydrate crystalline form may have a DSC endotherm onset at 108° C., with the endotherm peak positioned at 124° C.

Crystalline solid forms termed a "solvate," or "hydrate" are not meant to be limiting. For example, a solvate or hydrate can comprise a combination of water and solvent in the crystalline solid form.

The term "type," "form," and "pattern" are meant to be used interchangeably and are meant to refer to a particular crystalline material with properties described herein. For example, "crystalline hydrate Type A," "crystalline hydrate Form A," and "XRPD Pattern A" refer to the same crystalline matter.

The term "about" when referring to a number or a numerical range means that the number or numerical range referred to is an approximation within experimental variability (or within statistical experimental error), and thus the number or numerical range, in some instances, will vary between 1% and 15% of the stated number or numerical range.

The term "substantially similar" as used herein means an analytical spectrum, such as XRPD pattern, DSC thermogram, or TGA thermogram, which resembles the reference spectrum to a great degree in both the peak locations and peak intensity.

Characterization of Compounds and Solid State Forms

In one embodiment, the present invention provides solid state forms of Compound 1, Compound 2, Compound 3, Compound 4, Compound 5, and Compound 6. In one embodiment, the crystalline forms are characterized by the interlattice plane intervals determined by a X-ray powder diffraction (XRPD) diffractogram. The diffractogram is typically represented by a diagram plotting the intensity of the peaks versus the location of the peaks, i.e., diffraction angle 2Θ (two-theta) in degrees. The characteristic peaks of a given compound can be selected according to the peak locations and their relative intensity to distinguish compounds and crystalline structures from others. Amorphous solid state forms were also characterized by XRPD. Amorphous solid state forms exhibit an absence of interlattice plane intervals.

Both crystalline and amorphous solid state forms were identified for Compound 2, Compound 4, Compound 5, and Compound 6. Amorphous solid state forms as described herein are specifically denoted as such. For example, the language "solid state form of Compound 2" is meant to describe a crystalline form of Compound 2 unless specified as an amorphous solid state form.

Those skilled in the art recognize that the measurements of the XRD peak locations and/or intensity for a given crystalline form of the same compound will vary within a margin of error. The values of degree 2Θ allow appropriate error margins. Typically, the error margins are represented by "±". For example, the degree 2Θ of "8.716±0.3" denotes a range from 8.716'°±0.3, i.e., 9.016, to 8.716-0.3, i.e., 8.416. Depending on the sample preparation techniques, the calibration techniques applied to the instruments, human operational variation, and etc., those skilled in the art recognize that the margin of error for a XRD can be ±0.5; ±0.4; ±0.3; ±0.2; ±0.1; ±0.05; or less. Additional details of the methods and equipment used for the XRD analysis are described in the Examples section.

In one embodiment, the crystalline forms are characterized by Differential Scanning Calorimetry (DSC) and Thermogravimetric Analysis (TGA). The DSC thermogram is typically expressed by a diagram plotting the normalized heat flow in units of Watts/gram ("W/g") versus the measured sample temperature in degree C. The DSC thermogram is generally evaluated for extrapolated onset and end (outset) temperatures, peak temperature, and heat of fusion. The single maximum value of a DSV thermogram is often used as the characteristic peak to distinguish one crystalline form from another crystalline form. The TGA thermogram is typically expressed by a diagram plotting the weight loss percentage (%) versus the measured sample temperature in degree C. In the figures disclosed herein, DSC and TGA thermograms have been plotted sharing an X axis (temperature), but have distinct Y axes of weight % and heat flow corresponding respectively to TGA and DSC measurements.

Those skilled in the art recognize that the measurements of the DSC and TGA thermograms for a given crystalline form of the same compound will vary within a margin of error. The values of a single maximum value, expressed in degree C., allow appropriate error margins. Typically, the error margins are represented by "±". For example, the single maximum value of "53.1° C.±10.0" denotes a range from 53.1° C.±10.0, i.e., 63.1° C., to about 53.1° C.-10.0, i.e., 43.1° C. Depending on the sample preparation techniques, crystallization conditions, calibration techniques applied to the instruments, human operational variations, and etc., those skilled in the art recognize that the appropriate margin of error for a single maximum value can be ±10.0; ±7.5; ±5.0; ±2.5; ±2; ±1.5; ±1; ±0.5; or less for any of the powder diffraction reflections described herein.

Additional details of the methods and equipment used for the DSC and TGA thermogram analysis are described in the Examples section.

Compound 1

In some embodiments, the present invention provides an amorphous solid state of (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide, also known as Compound 1. In some embodiments, the amorphous solid state of Compound 1 exhibits the X-ray powder diffraction pattern substantially similar to that shown in FIG. 1.

Figure 2:
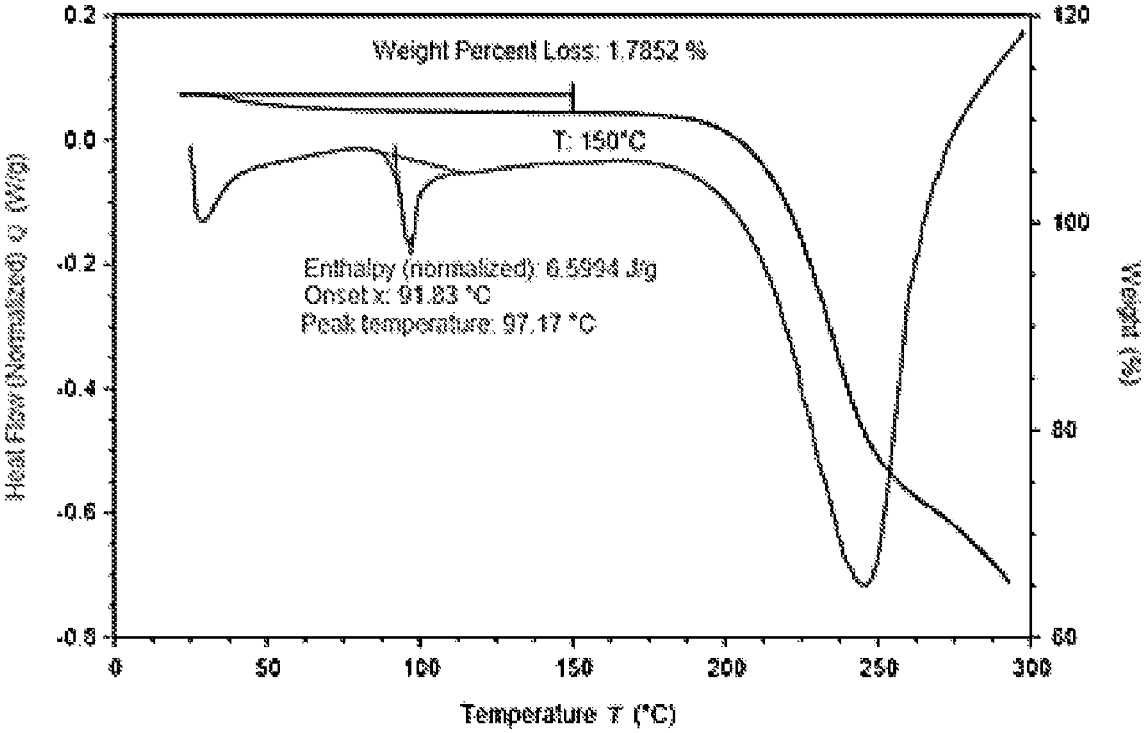
FIG. 2 shows a differential scanning calorimetry and thermogravimetric analysis of amorphous Compound 1.

In some embodiments, the amorphous solid state of Compound 1 exhibits a DSC thermogram substantially similar to that shown in FIG. 2. In some embodiments, the amorphous solid state of Compound 1 exhibits a DSC endotherm at 97.2° C.±5.0. In certain embodiments, the margin of error for the endotherms of the amorphous solid state of Compound 1 are selected from ±15.0; ±10.0; ±5.0; and ±2.0.

In some embodiments, the amorphous solid state of Compound 1 exhibits a TGA thermogram substantially similar to that shown in FIG. 2. In some embodiments, the amorphous solid state of Compound 1 exhibits TGA weight loss of 1.8%±0.5 at 150° C.±10.0. In certain embodiments, the margin of error for the TGA weight loss for the amorphous solid state of Compound 1 is selected from +5.0; ±2.0; ±1.0; ±0.5; and ±0.1.

In some embodiments, provided herein is a composition wherein the amorphous solid state of Compound 1 is substantially free of crystalline forms. In some embodiments, the amount of crystalline forms is 20% (w/w) or less. In some embodiments, the amount of crystalline forms is 15% (w/w) or less. In some embodiments, the amount of crystalline forms is 10% (w/w) or less. In some embodiments, the amount of crystalline forms is 5% (w/w) or less. In some embodiments, the amount of crystalline forms is 1% (w/w) or less.

Compound 2

In some embodiments, the present invention provides a crystalline solid state of (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide hydrochloride, also known as Compound 2. In some embodiments, the crystalline solid state of Compound 2 exhibits the X-ray powder diffraction pattern substantially similar to that shown in FIG. 3.

In some embodiments, the present invention provides a crystalline solid state form of Compound 2. In some embodiments, the solid state form exhibits an X-ray powder diffraction reflection at a 2-theta value of 19.7°±0.3. In some embodiments, the solid form exhibits an X-ray powder diffraction reflection at a 2-theta value of 11.1°±0.3 and 21.2°±0.3. In some embodiments, the solid form exhibits an X-ray powder diffraction reflection at a 2-theta value of 15.8°±0.3 and 22.0°±0.3. In some embodiments, the solid form exhibits an X-ray powder diffraction reflection at a 2-theta value of 13.9°±0.3, 18.5°±0.3, 21.7°±0.3, and 22.5°±0.3. In some embodiments, the solid form exhibits an X-ray powder diffraction reflection at a 2-theta value of 99.7°±0.3, 23.3°±0.3, and 23.8°±0.3.

In some embodiments, the solid form exhibits at least one X-ray powder diffraction reflection selected from 9.7°±0.3, 11.1°±0.3, 13.9°±0.3, 15.8°±0.3, 18.5°±0.3, 19.7°±0.3, 21.2°±0.3, 21.7°±0.3, 22.0°±0.3, 22.5°±0.3, 23.3°±0.3, and 23.8°±0.3. In some embodiments, the solid form exhibits at least one X-ray powder diffraction reflection selected from 20.3°±0.2, 23.4°±0.2, and 24.0°±0.2. In some embodiments, the solid form exhibits at least two X-ray powder diffraction reflections selected from 9.7°±0.3, 11.1°±0.3, 13.9°±0.3, 15.8°±0.3, 18.5°±0.3, 19.7°±0.3, 21.2°±0.3, 21.7°±0.3, 22.0°±0.3, 22.5°±0.3, 23.3°±0.3, and 23.8°±0.3. In some embodiments, the solid form exhibits at least three X-ray powder diffraction reflections selected from 9.7°±0.3, 11.1°±0.3, 13.9°±0.3, 15.8°±0.3, 18.5°±0.3, 19.7°±0.3, 21.2°±0.3, 21.7°±0.3, 22.0°±0.3, 22.5°±0.3, 23.3°±0.3, and 23.8°±0.3. In some embodiments, the solid form exhibits at least four X-ray powder diffraction reflections selected from 9.7°±0.3, 11.1°±0.3, 13.9°±0.3, 15.8°±0.3, 18.5°±0.3, 19.7°±0.3, 21.2°±0.3, 21.7°±0.3, 22.0°±0.3, 22.5°±0.3, 23.3°±0.3, and 23.8°±0.3. In some embodiments, the solid form exhibits at least five X-ray powder diffraction reflections selected from 9.7°±0.3, 11.1°±0.3, 13.9°±0.3, 15.8°±0.3, 18.5°±0.3, 19.7°±0.3, 21.2°±0.3, 21.7°±0.3, 22.0°±0.3, 22.5°±0.3, 23.3°±0.3, and 23.8°±0.3. In some embodiments, the solid form exhibits at least six X-ray powder diffraction reflections selected from 9.7°±0.3, 11.1°±0.3, 13.9°±0.3, 15.8°±0.3, 18.5°±0.3, 19.7°±0.3, 21.2°±0.3, 21.7°±0.3, 22.0°±0.3, 22.5°±0.3, 23.3°±0.3, and 23.8°±0.3. In certain embodiments, the margin of error for any one of the reflections of Compound 2 is selected from ±0.5; ±0.4; ±0.3; ±0.2; ±0.1; and ±0.05. In some embodiments, Compound 2 exhibits the X-ray powder diffraction pattern substantially similar to that shown in FIG. 3. In some embodiments, Compound 2 exhibits at least one of the X-ray powder diffraction pattern reflections in Table 1.

TABLE 1

Peak listing for the X-ray powder diffractogram of the crystalline solid state form of Compound 2.

| 2-Theta | d(Å) | Relative Intensity % |
|---|---|---|
| 6.83 | 12.930 | 5 |
| 7.76 | 11.378 | 5 |
| 9.77 | 9.042 | 22 |
| 10.67 | 8.287 | 4 |

TABLE 1-continued

Peak listing for the X-ray powder diffractogram of the crystalline solid state form of Compound 2.

| 2-Theta | d(Å) | Relative Intensity % |
|---|---|---|
| 11.21 | 7.886 | 63 |
| 11.81 | 7.485 | 7 |
| 12.43 | 7.113 | 19 |
| 12.68 | 6.973 | 3 |
| 13.23 | 6.688 | 5 |
| 13.97 | 6.335 | 18 |
| 14.39 | 6.149 | 4 |
| 14.50 | 6.102 | 4 |
| 14.85 | 5.962 | 7 |
| 15.32 | 5.780 | 6 |
| 15.58 | 5.683 | 7 |
| 15.86 | 5.582 | 27 |
| 16.95 | 5.226 | 19 |
| 17.42 | 5.086 | 14 |
| 17.81 | 4.975 | 4 |
| 18.59 | 4.769 | 37 |
| 19.55 | 4.538 | 16 |
| 19.72 | 4.499 | 100 |
| 20.28 | 4.374 | 23 |
| 20.64 | 4.299 | 11 |
| 20.72 | 4.282 | 16 |
| 21.24 | 4.180 | 73 |
| 21.75 | 4.083 | 18 |
| 22.11 | 4.018 | 32 |
| 22.35 | 3.975 | 11 |
| 22.55 | 3.939 | 18 |
| 23.00 | 3.863 | 8 |
| 23.23 | 3.826 | 18 |
| 23.31 | 3.813 | 21 |
| 23.38 | 3.802 | 23 |
| 23.66 | 3.758 | 13 |
| 23.86 | 3.727 | 19 |
| 23.95 | 3.713 | 25 |
| 25.09 | 3.546 | 9 |
| 25.40 | 3.504 | 4 |
| 26.14 | 3.406 | 8 |
| 26.30 | 3.386 | 14 |
| 26.66 | 3.341 | 12 |
| 27.27 | 3.268 | 5 |
| 27.63 | 3.225 | 9 |
| 27.90 | 3.196 | 8 |
| 28.07 | 3.176 | 10 |
| 28.38 | 3.142 | 5 |
| 28.58 | 3.121 | 7 |
| 29.02 | 3.074 | 4 |
| 29.37 | 3.039 | 6 |
| 29.64 | 3.012 | 5 |
| 29.78 | 2.998 | 9 |
| 29.97 | 2.979 | 4 |
| 30.27 | 2.951 | 6 |

Figure 4:
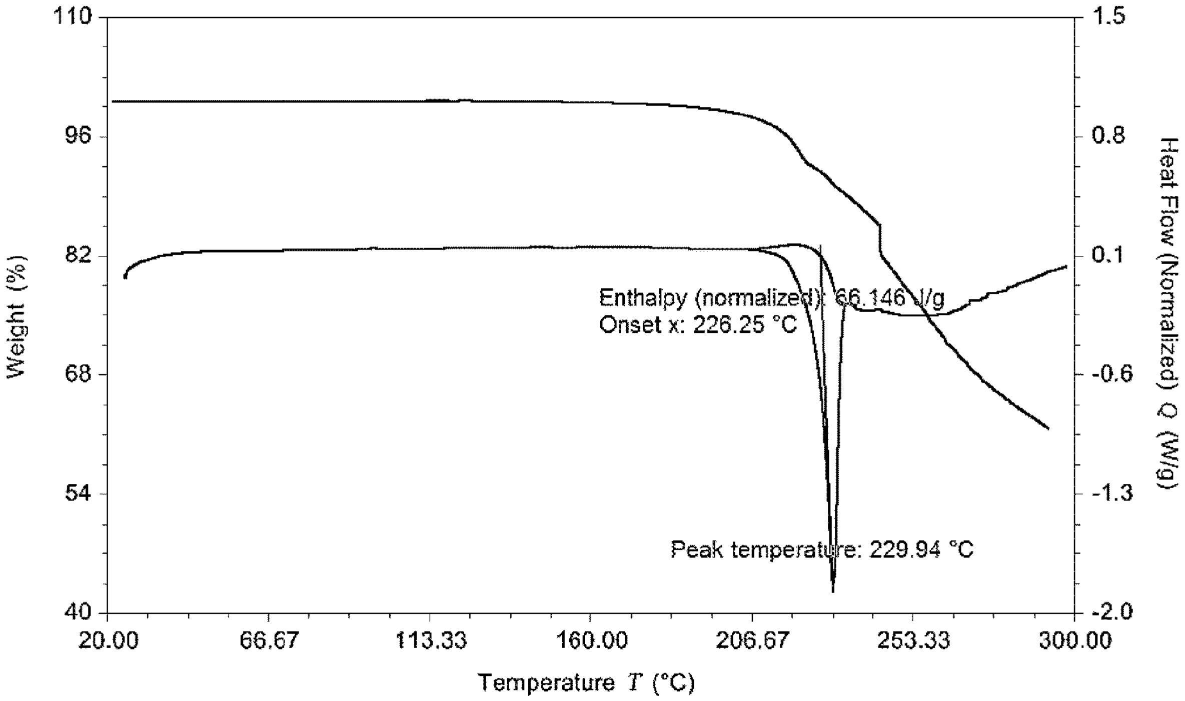
FIG. 4 shows a differential scanning calorimetry and thermogravimetric analysis of crystalline Compound 2.

In some embodiments, the crystalline solid state of Compound 2 exhibits a DSC thermogram substantially similar to that shown in FIG. 4. In some embodiments, the crystalline solid state of Compound 2 exhibits a DSC endotherm at 229.9° C.±5.0. In certain embodiments, the margin of error for the endotherms of the crystalline solid state of Compound 2 are selected from ±15.0; ±10.0; ±5.0; and ±2.0.

In some embodiments, the crystalline solid state of Compound 2 exhibits a TGA thermogram substantially similar to that shown in FIG. 4. In some embodiments, the crystalline solid state of Compound 2 exhibits less than 1.0%±0.5 weight loss up to 160° C. 10.0. In certain embodiments, the margin of error for the TGA weight loss for the crystalline solid state of Compound 2 is selected from +5.0; ±2.0; ±1.0; ±0.5; and ±0.1.

In some embodiments, provided herein is a composition wherein the crystalline solid state form of Compound 2 is substantially free of other crystalline or amorphous forms. In some embodiments, the amount of other crystalline or amorphous forms is 20% (w/w) or less. In some embodiments, the amount of other crystalline or amorphous forms is 15% (w/w) or less. In some embodiments, the amount of other crystalline or amorphous forms is 10% (w/w) or less. In some embodiments, the amount of other crystalline or amorphous forms is 5% (w/w) or less. In some embodiments, the amount of other crystalline or amorphous forms is 1% (w/w) or less.

Compound 3

In some embodiments, the present invention provides a crystalline solid state of (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide hydrobromide, also known as Compound 3. In some embodiments, the crystalline solid state of Compound 3 exhibits the X-ray powder diffraction pattern substantially similar to that shown in FIG. 5.

In some embodiments, the present invention provides a crystalline solid state form of Compound 3. In some embodiments, the solid state form exhibits an X-ray powder diffraction reflection at a 2-theta value of 21.9°±0.3. In some embodiments, the solid form exhibits an X-ray powder diffraction reflection at a 2-theta value of 19.7°±0.3 and 21.1°±0.3. In some embodiments, the solid form exhibits an X-ray powder diffraction reflection at a 2-theta value of 19.3°±0.3, 20.1°±0.3, and 21.3°±0.3. In some embodiments, the solid form exhibits an X-ray powder diffraction reflection at a 2-theta value of 12.2°±0.3, 23.2°±0.3, and 24.0°±0.3. In some embodiments, the solid form exhibits an X-ray powder diffraction reflection at a 2-theta value of 17.1°±0.3, 27.3°±0.3, and 28.7°±0.3.

In some embodiments, the solid form exhibits at least one X-ray powder diffraction reflection selected from 12.2°±0.3, 17.1°±0.3, 19.7°±0.3, 21.1°±0.3, 21.9°±0.3, 23.2°±0.3, 24.0°±0.3, 27.3°±0.3, and 28.7°±0.3. In some embodiments, the solid form exhibits at least two X-ray powder diffraction reflections selected from 12.2°±0.3, 17.1°±0.3, 19.7°±0.3, 21.1°±0.3, 21.9°±0.3, 23.2°±0.3, 24.0°±0.3, 27.3°±0.3, and 28.7°±0.3. In some embodiments, the solid form exhibits at least three X-ray powder diffraction reflections selected from 12.2°±0.3, 17.1°±0.3, 19.7°±0.3, 21.1°±0.3, 21.9°±0.3, 23.2°±0.3, 24.0°±0.3, 27.3°±0.3, and 28.7°±0.3. In some embodiments, the solid form exhibits at least four X-ray powder diffraction reflections selected from 12.2°±0.3, 17.1°±0.3, 19.7°±0.3, 21.1°±0.3, 21.9°±0.3, 23.2°±0.3, 24.0°±0.3, 27.3°±0.3, and 28.7°±0.3. In some embodiments, the solid form exhibits at least five X-ray powder diffraction reflections selected from 12.2°±0.3, 17.1°±0.3, 19.7°±0.3, 21.1°±0.3, 21.9°±0.3, 23.2°±0.3, 24.0°±0.3, 27.3°±0.3, and 28.7°±0.3. In some embodiments, the solid form exhibits at least six X-ray powder diffraction reflections selected from 12.2°±0.3, 17.1°±0.3, 19.7°±0.3, 21.1°±0.3, 21.9°±0.3, 23.2°±0.3, 24.0°±0.3, 27.3°±0.3, and 28.7°±0.3. In certain embodiments, the margin of error for any one of the reflections of Compound 3 is selected from ±0.5; ±0.4; ±0.3; ±0.2; ±0.1; and ±0.05. In some embodiments, Compound 3 exhibits the X-ray powder diffraction pattern substantially similar to that shown in FIG. 5. In some embodiments, Compound 3 exhibits at least one of the X-ray powder diffraction pattern reflections in Table 2.

TABLE 2

Peak listing for the X-ray powder diffractogram of the crystalline solid state form of Compound 3.

| 2-Theta | d(Å) | Relative Intensity % |
|---|---|---|
| 7.649 | 11.54848 | 15.2 |
| 11.415 | 7.74532 | 15.2 |
| 12.158 | 7.27397 | 19.8 |
| 13.355 | 6.62441 | 9 |
| 13.83 | 6.39824 | 11.3 |
| 14.216 | 6.22494 | 8.2 |
| 14.792 | 5.98394 | 8.6 |
| 15.349 | 5.76815 | 11.7 |
| 15.601 | 5.6755 | 7.9 |
| 16.649 | 5.32048 | 11.3 |
| 17.086 | 5.18532 | 17.3 |
| 17.535 | 5.05357 | 6.5 |
| 18.108 | 4.89503 | 17 |
| 19.273 | 4.60158 | 29.7 |
| 19.696 | 4.50387 | 32.3 |
| 20.068 | 4.42108 | 27.4 |
| 21.082 | 4.21061 | 47.7 |
| 21.273 | 4.17336 | 25.6 |
| 21.516 | 4.12666 | 17.6 |
| 21.867 | 4.06122 | 100 |
| 22.241 | 3.99374 | 15.4 |
| 22.699 | 3.91419 | 12.2 |
| 23.152 | 3.83867 | 20.8 |
| 23.973 | 3.70899 | 20.9 |
| 24.813 | 3.58535 | 7 |
| 26.161 | 3.40356 | 10.2 |
| 26.83 | 3.32016 | 11.2 |
| 27.324 | 3.26128 | 18.4 |
| 27.865 | 3.19921 | 14.4 |
| 28.368 | 3.14365 | 6.7 |
| 28.666 | 3.11159 | 17.4 |
| 29.025 | 3.0739 | 13.8 |
| 29.333 | 3.04233 | 7.2 |
| 30.401 | 2.93788 | 10.1 |
| 30.753 | 2.90499 | 8.7 |
| 31.012 | 2.88135 | 13.1 |
| 31.613 | 2.82796 | 7.6 |
| 32.062 | 2.78932 | 11.8 |
| 32.349 | 2.76528 | 6.4 |
| 32.786 | 2.72935 | 7.5 |
| 33.987 | 2.63561 | 14.1 |
| 34.566 | 2.59278 | 7.5 |
| 35.355 | 2.5367 | 13.9 |
| 35.692 | 2.51357 | 14.2 |
| 36.203 | 2.47925 | 5.5 |
| 36.899 | 2.43406 | 9.4 |
| 37.684 | 2.38515 | 5.3 |
| 39.663 | 2.27055 | 5.6 |

Figure 6:
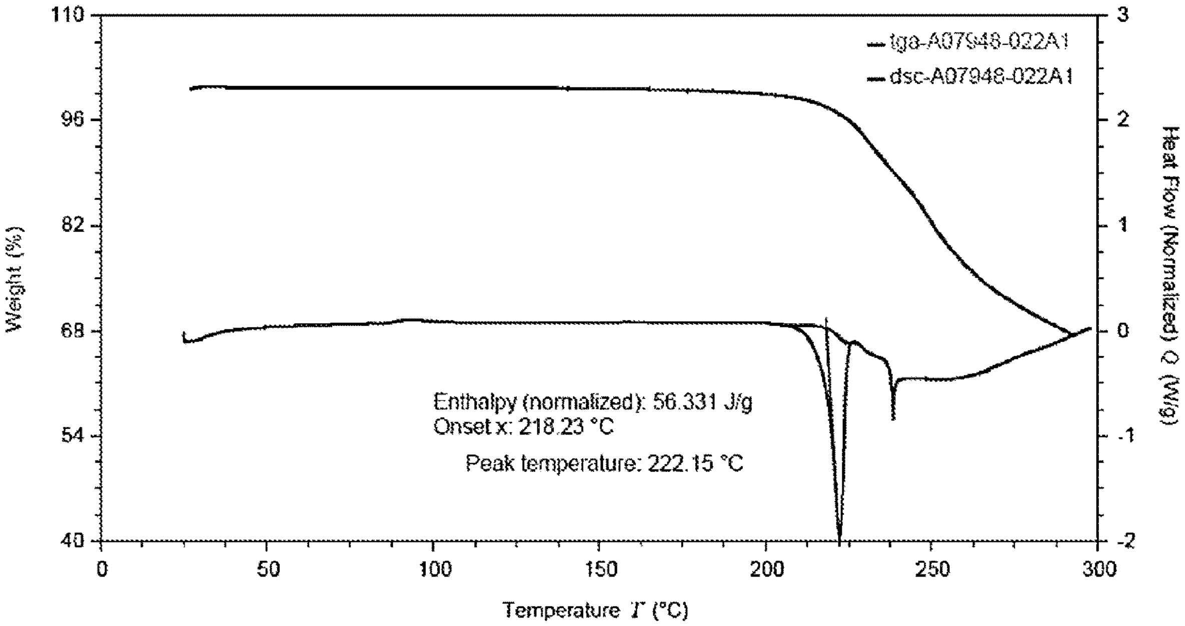
FIG. 6 shows a differential scanning calorimetry and thermogravimetric analysis of crystalline Compound 3.

In some embodiments, the crystalline solid state of Compound 3 exhibits a DSC thermogram substantially similar to that shown in FIG. 6. In some embodiments, the crystalline solid state of Compound 3 exhibits a DSC endotherm at 222.2° C.±5.0. In certain embodiments, the margin of error for the endotherms of the crystalline solid state of Compound 3 are selected from ±15.0; ±10.0; ±5.0; and ±2.0.

In some embodiments, the crystalline solid state of Compound 3 exhibits a TGA thermogram substantially similar to that shown in FIG. 6. In some embodiments, the crystalline solid state of Compound 3 exhibits less than 1.0%±0.5 weight loss up to 150° C. 10.0. In certain embodiments, the margin of error for the TGA weight loss for the crystalline solid state of Compound 3 is selected from +5.0; ±2.0; ±1.0; ±0.5; and ±0.1.

In some embodiments, provided herein is a composition wherein the crystalline solid state form of Compound 3 is substantially free of other crystalline or amorphous forms. In some embodiments, the amount of other crystalline or amorphous forms is 20% (w/w) or less. In some embodiments, the amount of other crystalline or amorphous forms is 15% (w/w) or less. In some embodiments, the amount of other crystalline or amorphous forms is 10% (w/w) or less. In some embodiments, the amount of other crystalline or amorphous forms is 5% (w/w) or less. In some embodiments, the amount of other crystalline or amorphous forms is 1% (w/w) or less.

Compound 4

In some embodiments, the present invention provides a crystalline solid state of (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide 4-methylbenzenesulfonate, also known as Compound 4. In some embodiments, the crystalline solid state of Compound 4 is crystalized in the presence of MTBE (Form I) and exhibits the X-ray powder diffraction pattern substantially similar to that shown in FIG. 6. In some embodiments, the crystalline solid state of Compound 4 is crystalized in the presence of acetone (Form II) and exhibits the X-ray powder diffraction pattern substantially similar to that shown in FIG. 7.

Compound 4—Form I Crystalized with MTBE

In some embodiments, the present invention provides a crystalline solid state form of Compound 4 Form I, which is crystalized in the presence of MTBE. In some embodiments, the solid form exhibits an X-ray powder diffraction reflection at a 2-theta value of 6.1°±0.3. In some embodiments, the solid form exhibits an X-ray powder diffraction reflection at a 2-theta value of 15.0°±0.3 and 17.9°±0.3. In some embodiments, the solid form exhibits an X-ray powder diffraction reflection at a 2-theta value of 5.7°±0.3, 7.2°±0.3, and 18.5°±0.3. In some embodiments, the solid form exhibits an X-ray powder diffraction reflection at a 2-theta value of 9.3°±0.3, 12.1°±0.3, 12.7°±0.3, and 19.9°±0.3. In some embodiments, the solid form exhibits an X-ray powder diffraction reflection at a 2-theta value of 14.5°±0.3, 15.5°±0.3, and 16.6°±0.3.

In some embodiments, the solid form exhibits at least one X-ray powder diffraction reflection selected from 5.7°±0.3, 6.1°±0.3, 7.2°±0.3, 9.3°±0.3, 12.1°±0.3, 12.7°±0.3, 14.5°±0.3, 15.0°±0.3, 15.5°±0.3, 16.6°±0.3, 17.9°±0.3, 18.5°±0.3, and 19.9°±0.3. In some embodiments, the solid form exhibits at least two X-ray powder diffraction reflections selected from 5.7°±0.3, 6.1°±0.3, 7.2°±0.3, 9.3°±0.3, 12.1°±0.3, 12.7°±0.3, 14.5°±0.3, 15.0°±0.3, 15.5°±0.3, 16.6°±0.3, 17.9°±0.3, 18.5°±0.3, and 19.9°±0.3. In some embodiments, the solid form exhibits at least three X-ray powder diffraction reflections selected from 5.7°±0.3, 6.1°±0.3, 7.2°±0.3, 9.3°±0.3, 12.1°±0.3, 12.7°±0.3, 14.5°±0.3, 15.0°±0.3, 15.5°±0.3, 16.6°±0.3, 17.9°±0.3, 18.5°±0.3, and 19.9°±0.3. In some embodiments, the solid form exhibits at least four X-ray powder diffraction reflections selected from 5.7°±0.3, 6.1°±0.3, 7.2°±0.3, 9.3°±0.3, 12.1°±0.3, 12.7°±0.3, 14.5°±0.3, 15.0°±0.3, 15.5°±0.3, 16.6°±0.3, 17.9°±0.3, 18.5°±0.3, and 19.9°±0.3. In some embodiments, the solid form exhibits at least five X-ray powder diffraction reflections selected from 5.7°±0.3, 6.1°±0.3, 7.2°±0.3, 9.3°±0.3, 12.1°±0.3, 12.7°±0.3, 14.5°±0.3, 15.0°±0.3, 15.5°±0.3, 16.6°±0.3, 17.9°±0.3, 18.5°±0.3, and 19.9°±0.3. In some embodiments, the solid form exhibits at least six X-ray powder diffraction reflections selected from 5.7°±0.3, 6.1°±0.3, 7.2°±0.3, 9.3°±0.3, 12.1°±0.3, 12.7°±0.3, 14.5°±0.3, 15.0°±0.3, 15.5°±0.3, 16.6°±0.3, 17.9°±0.3, 18.5°±0.3, and 19.9°±0.3. In certain embodiments, the margin of error for any one of the reflections of Compound 4 is selected from ±0.5; ±0.4; ±0.3; ±0.2; ±0.1; and ±0.05. In some embodiments, Compound 4 Form I exhibits the X-ray powder diffraction pattern substantially similar to that shown in FIG. 7. In some embodiments, Compound 4 Form I exhibits at least one of the X-ray powder diffraction pattern reflections in Table 3.

TABLE 3

Peak listing for the X-ray powder diffractogram of the crystalline solid state form of Compound 4 Form I.

| 2-Theta | d(Å) | Relative Intensity % |
|---|---|---|
| 5.695 | 15.5063 | 28.4 |
| 6.139 | 14.385 | 100 |
| 7.175 | 12.3104 | 28.9 |
| 9.256 | 9.54655 | 12.8 |
| 11.109 | 7.95846 | 10.9 |
| 12.119 | 7.29721 | 12.9 |
| 12.684 | 6.97336 | 12.7 |
| 14.483 | 6.1108 | 11.5 |
| 14.955 | 5.91915 | 31.7 |
| 15.48 | 5.71969 | 11.2 |
| 16.582 | 5.34179 | 15.7 |
| 17.889 | 4.95435 | 47.1 |
| 18.548 | 4.77973 | 18 |
| 19.898 | 4.4584 | 12.2 |
| 20.883 | 4.25035 | 10.8 |
| 21.671 | 4.09752 | 9.5 |
| 23.462 | 3.78873 | 7.9 |
| 24.827 | 3.58341 | 7.8 |
| 27.07 | 3.29133 | 7.8 |
| 30.156 | 2.96118 | 7.5 |
| 31.356 | 2.85056 | 4.6 |
| 33.162 | 2.69926 | 5.2 |

In some embodiments, provided herein is a composition wherein the crystalline solid state form of Compound 4 Form I is substantially free of other crystalline or amorphous forms. In some embodiments, the amount of other crystalline or amorphous forms is 20% (w/w) or less. In some embodiments, the amount of other crystalline or amorphous forms is 15% (w/w) or less. In some embodiments, the amount of other crystalline or amorphous forms is 10% (w/w) or less. In some embodiments, the amount of other crystalline or amorphous forms is 5% (w/w) or less. In some embodiments, the amount of other crystalline or amorphous forms is 1% (w/w) or less.

Compound 4—Form II Crystalized with Acetone

In some embodiments, the present invention provides a crystalline solid state form of Compound 4 Form II, which is crystalized in the presence of acetone. In some embodiments, the present invention provides a crystalline solid state form of Compound 4 Form II. In some embodiments, the solid form exhibits an X-ray powder diffraction reflection at a 2-theta value of 6.8°±0.3. In some embodiments, the solid form exhibits an X-ray powder diffraction reflection at a 2-theta value of 5.2°±0.3, 6.1°±0.3, and 18.8°±0.3. In some embodiments, the solid form exhibits an X-ray powder diffraction reflection at a 2-theta value of 16.3°±0.3, 17.1°±0.3, and 21.1°±0.3. In some embodiments, the solid form exhibits an X-ray powder diffraction reflection at a 2-theta value of 12.5°±0.3, 17.2°±0.3, 18.5°±0.3, and 19.2°±0.3. In some embodiments, the solid form exhibits an X-ray powder diffraction reflection at a 2-theta value of 10.5°±0.3, 11.9°±0.3, and 12.9°±0.3.

In some embodiments, the solid form exhibits at least one X-ray powder diffraction reflection selected from 5.2°±0.3, 6.1°±0.3, 6.8°±0.3, 10.5°±0.3, 11.9°±0.3, 12.5°±0.3, 12.9°±0.3, 16.3°±0.3, 17.1°±0.3, 17.2°±0.3, 18.5°±0.3, 18.8°±0.3, 19.2°±0.3, and 21.1°±0.3. In some embodiments, the solid form exhibits at least two X-ray powder diffraction reflections selected from 5.2°±0.3, 6.1°±0.3, 6.8°±0.3, 10.5°±0.3, 11.9°±0.3, 12.5°±0.3, 12.9°±0.3, 16.3°±0.3, 17.1°±0.3, 17.2°±0.3, 18.5°±0.3, 18.8°±0.3, 19.2°±0.3, and 21.1°±0.3. In some embodiments, the solid form exhibits at least three X-ray powder diffraction reflections selected from 5.2°±0.3, 6.1°±0.3, 6.8°±0.3, 10.5°±0.3, 11.9°±0.3, 12.5°±0.3, 12.9°±0.3, 16.3°±0.3, 17.1°±0.3, 17.2°±0.3, 18.5°±0.3, 18.80°±0.3, 19.2°±0.3, and 21.10±0.3. In some embodiments, the solid form exhibits at least four X-ray powder diffraction reflections selected from 5.2°±0.3, 6.1°±0.3, 6.8°±0.3, 10.5°±0.3, 11.9°±0.3, 12.5°±0.3, 12.9°±0.3, 16.3°±0.3, 17.1°±0.3, 17.20°±0.3, 18.5°±0.3, 18.80°±0.3, 19.20°±0.3, and 21.10±0.3. In some embodiments, the solid form exhibits at least five X-ray powder diffraction reflections selected from 5.2°±0.3, 6.1°±0.3, 6.8°±0.3, 10.5°±0.3, 11.9°±0.3, 12.5°±0.3, 12.9°±0.3, 16.3°±0.3, 17.1°±0.3, 17.2°±0.3, 18.5°±0.3, 18.8°±0.3, 19.2°±0.3, and 21.1°±0.3. In some embodiments, the solid form exhibits at least six X-ray powder diffraction reflections selected from 5.2°±0.3, 6.1°±0.3, 6.8°±0.3, 10.5°±0.3, 11.9°±0.3, 12.5°±0.3, 12.9°±0.3, 16.3°±0.3, 17.1°±0.3, 17.2°±0.3, 18.5°±0.3, 18.8°±0.3, 19.2°±0.3, and 21.1°±0.3. In certain embodiments, the margin of error for any one of the reflections of Compound 4 is selected from ±0.5; ±0.4; ±0.3; ±0.2; ±0.1; and ±0.05. In some embodiments, Compound 4 Form II exhibits the X-ray powder diffraction pattern substantially similar to that shown in FIG. 8. In some embodiments, Compound 4 Form II exhibits at least one of the X-ray powder diffraction pattern reflections in Table 4.

TABLE 4

Peak listing for the X-ray powder diffractogram of the crystalline solid state form of Compound 4 Form II.

| 2-Theta | d(Å) | Relative Intensity % |
|---|---|---|
| 5.226 | 16.89774 | 96.3 |
| 6.065 | 14.56103 | 87.7 |
| 6.836 | 12.92035 | 100 |
| 10.482 | 8.43312 | 38.3 |
| 11.919 | 7.41924 | 43.1 |
| 12.469 | 7.09327 | 50 |
| 12.854 | 6.88138 | 41.3 |
| 13.951 | 6.34296 | 35.1 |
| 14.848 | 5.96163 | 29.8 |
| 16.31 | 5.43021 | 47.9 |
| 17.082 | 5.18654 | 45.8 |
| 17.271 | 5.13035 | 53.8 |
| 18.52 | 4.78701 | 56.8 |
| 18.845 | 4.70517 | 76.4 |
| 19.19 | 4.62145 | 52.3 |
| 21.12 | 4.20325 | 48.3 |
| 24.677 | 3.60482 | 26 |

In some embodiments, provided herein is a composition wherein the crystalline solid state form of Compound 4 Form II is substantially free of other crystalline or amorphous forms. In some embodiments, the amount of other crystalline or amorphous forms is 20% (w/w) or less. In some embodiments, the amount of other crystalline or amorphous forms is 15% (w/w) or less. In some embodiments, the amount of other crystalline or amorphous forms is 10% (w/w) or less. In some embodiments, the amount of other crystalline or amorphous forms is 5% (w/w) or less. In some embodiments, the amount of other crystalline or amorphous forms is 1% (w/w) or less.

Compound 5

In some embodiments, the present invention provides a crystalline solid state of (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide phosphate, also known as Compound 5. In some embodiments, the crystalline solid state of Compound 5 exhibits the X-ray powder diffraction pattern substantially similar to that shown in FIG. 9.

In some embodiments, the solid form exhibits an X-ray powder diffraction reflection at a 2-theta value of 6.9°±0.3. In some embodiments, the solid form exhibits an X-ray powder diffraction reflection at a 2-theta value of 18.3°±0.3 and 24.0°±0.3. In some embodiments, the solid form exhibits an X-ray powder diffraction reflection at a 2-theta value of 9.1°±0.3, 20.7°±0.3, and 22.7°±0.3. In some embodiments, the solid form exhibits an X-ray powder diffraction reflection at a 2-theta value of 5.9°±0.3, 11.9°±0.3, 13.8°±0.3, and 21.9°±0.3. In some embodiments, the solid form exhibits an X-ray powder diffraction reflection at a 2-theta value of 19.2°±0.3, 20.4°±0.3, 25.8°±0.3, and 26.6°±0.3.

In some embodiments, the solid form exhibits at least one X-ray powder diffraction reflection selected from 5.9°±0.3, 6.9°±0.3, 9.1°±0.3, 11.9°±0.3, 13.8°±0.3, 18.3°±0.3, 19.2°±0.3, 20.4°±0.3, 20.7°±0.3, 21.9°±0.3, 22.7°±0.3, 24.0°±0.3, 25.8°±0.3, and 26.6°±0.3. In some embodiments, the solid form exhibits at least two X-ray powder diffraction reflections selected from 5.9°±0.3, 6.9°±0.3, 9.1°±0.3, 11.9°±0.3, 13.8°±0.3, 18.3°±0.3, 19.2°±0.3, 20.4°±0.3, 20.7°±0.3, 21.9°±0.3, 22.7°±0.3, 24.0°±0.3, 25.8°±0.3, and 26.6°±0.3. In some embodiments, the solid form exhibits at least three X-ray powder diffraction reflections selected from 5.9°±0.3, 6.9°±0.3, 9.1°±0.3, 11.9°±0.3, 13.8°±0.3, 18.3°±0.3, 19.2°±0.3, 20.4°±0.3, 20.7°±0.3, 21.9°±0.3, 22.7°±0.3, 24.0°±0.3, 25.8°±0.3, and 26.6°±0.3. In some embodiments, the solid form exhibits at least four X-ray powder diffraction reflections selected from 5.9°±0.3, 6.9°±0.3, 9.1°±0.3, 11.9°±0.3, 13.8°±0.3, 18.3°±0.3, 19.2°±0.3, 20.4°±0.3, 20.7°±0.3, 21.9°±0.3, 22.7°±0.3, 24.0°±0.3, 25.8°±0.3, and 26.6°±0.3. In some embodiments, the solid form exhibits at least five X-ray powder diffraction reflections selected from 5.9°±0.3, 6.9°±0.3, 9.1°±0.3, 11.9°±0.3, 13.8°±0.3, 18.3°±0.3, 19.2°±0.3, 20.4°±0.3, 20.7°±0.3, 21.9°±0.3, 22.7°±0.3, 24.0°±0.3, 25.8°±0.3, and 26.6°±0.3. In some embodiments, the solid form exhibits at least six X-ray powder diffraction reflections selected from 5.9°±0.3, 6.9°±0.3, 9.1°±0.3, 11.9°±0.3, 13.8°±0.3, 18.3°±0.3, 19.2°±0.3, 20.4°±0.3, 20.7°±0.3, 21.9°±0.3, 22.7°±0.3, 24.0°±0.3, 25.8°±0.3, and 26.60±0.3. In certain embodiments, the margin of error for any one of the reflections of Compound 5 is selected from ±0.5; ±0.4; ±0.3; ±0.2; ±0.1; and ±0.05. In some embodiments, Compound 5 exhibits the X-ray powder diffraction pattern substantially similar to that shown in FIG. 9. In some embodiments, Compound 5 exhibits at least one of the X-ray powder diffraction pattern reflections in Table 5.

TABLE 5

Peak listing for the X-ray powder diffractogram of the crystalline solid state form of Compound 5.

| 2-Theta | d(Å) | Relative Intensity % |
|---|---|---|
| 5.934 | 14.88229 | 17.2 |
| 6.904 | 12.79303 | 100 |
| 9.113 | 9.69687 | 29.9 |
| 10.726 | 8.24169 | 8 |
| 11.292 | 7.82983 | 8.7 |
| 11.949 | 7.4007 | 19.2 |
| 12.204 | 7.24664 | 11.8 |
| 12.77 | 6.92651 | 9.9 |
| 13.294 | 6.65484 | 11.1 |
| 13.828 | 6.39876 | 17.3 |

TABLE 5-continued

Peak listing for the X-ray powder diffractogram of the crystalline solid state form of Compound 5.

| 2-Theta | d(Å) | Relative Intensity % |
|---|---|---|
| 14.97 | 5.91335 | 13.3 |
| 15.799 | 5.60464 | 11.8 |
| 16.765 | 5.2838 | 10.3 |
| 17.251 | 5.13622 | 13.7 |
| 17.539 | 5.05253 | 13.8 |
| 18.287 | 4.84749 | 89.4 |
| 18.89 | 4.69407 | 13.8 |
| 19.19 | 4.62134 | 14.5 |
| 20.443 | 4.3408 | 14.7 |
| 20.742 | 4.27903 | 36 |
| 21.875 | 4.0598 | 21.7 |
| 22.685 | 3.91664 | 35.8 |
| 23.997 | 3.70535 | 56.1 |
| 24.938 | 3.56767 | 12.9 |
| 25.274 | 3.521 | 13 |
| 25.829 | 3.44652 | 14.4 |
| 26.636 | 3.34395 | 15 |
| 27.757 | 3.21145 | 12 |
| 29.411 | 3.03448 | 6.4 |
| 30.327 | 2.94491 | 7.4 |
| 31.593 | 2.8297 | 5.9 |
| 37.47 | 2.39825 | 5.2 |

Figure 10:
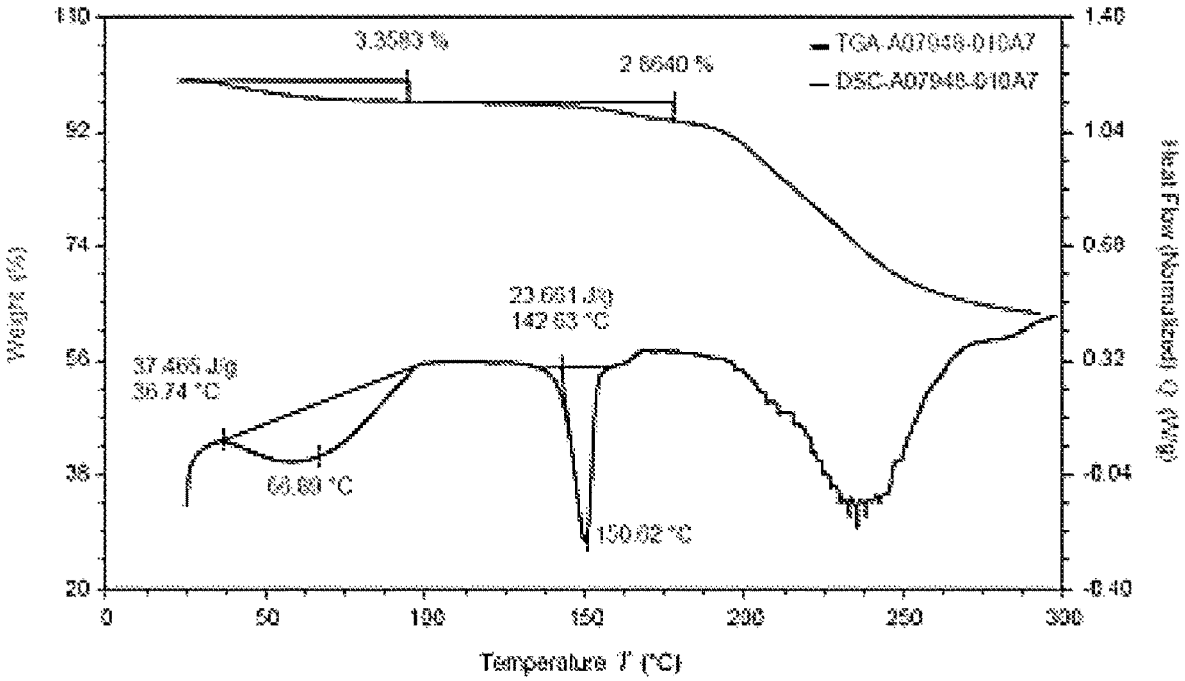
FIG. 10 shows a differential scanning calorimetry and thermogravimetric analysis of crystalline Compound 5.

In some embodiments, the crystalline solid state of Compound 5 exhibits a DSC thermogram substantially similar to that shown in FIG. 10. In some embodiments, the crystalline solid state of Compound 5 exhibits a DSC endotherm at 150.6° C.±5.0. In certain embodiments, the margin of error for the endotherms of the crystalline solid state of Compound 5 are selected from ±15.0; ±10.0; ±5.0; and ±2.0.

In some embodiments, the crystalline solid state of Compound 5 exhibits a TGA thermogram substantially similar to that shown in FIG. 10. In some embodiments, the crystalline solid state of Compound 5 exhibits less than 6.2%±0.5 weight loss up to 170° C.±10.0. In certain embodiments, the margin of error for the TGA weight loss for the crystalline solid state of Compound 5 is selected from ±5.0; ±2.0; ±1.0; ±0.5; and ±0.1.

In some embodiments, provided herein is a composition wherein the crystalline solid state form of Compound 5 is substantially free of other crystalline or amorphous forms. In some embodiments, the amount of other crystalline or amorphous forms is 20% (w/w) or less. In some embodiments, the amount of other crystalline or amorphous forms is 15% (w/w) or less. In some embodiments, the amount of other crystalline or amorphous forms is 10% (w/w) or less. In some embodiments, the amount of other crystalline or amorphous forms is 5% (w/w) or less. In some embodiments, the amount of other crystalline or amorphous forms is 1% (w/w) or less.

Compound 6

In some embodiments, the present invention provides a crystalline solid state of (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide sulfate, also known as Compound 6. In some embodiments, the crystalline solid state of Compound 6 is crystalized in the presence of acetonitrile (Form I). In some embodiments, the crystalline solid state of Compound 6 is crystalized in the presence of isopropyl alcohol (Form II).

Compound 6—Form I Crystalized with Acetonitrile

In some embodiments, the present invention provides a crystalline solid state form of Compound 6 Form I, which is crystalized in the presence of acetonitrile. In some embodiments, the solid form exhibits an X-ray powder diffraction reflection at a 2-theta value of In some embodiments, the solid form exhibits an X-ray powder diffraction reflection at a 2-theta value of 3.2°±0.3. In some embodiments, the solid form exhibits an X-ray powder diffraction reflection at a 2-theta value of 3.3°±0.3 and 6.8°±0.3. In some embodiments, the solid form exhibits an X-ray powder diffraction reflection at a 2-theta value of 4.6°±0.3 and 7.1°±0.3. In some embodiments, the solid form exhibits an X-ray powder diffraction reflection at a 2-theta value of 8.0°±0.3, 12.5°±0.3, 15.7°±0.3, 16.0°±0.3, and 19.9°±0.3.

In some embodiments, the solid form exhibits at least one X-ray powder diffraction reflection selected from 3.2°±0.3, 3.3°±0.3, 4.6°±0.3, 6.8°±0.3, 7.1°±0.3, 8.0°±0.3, 12.5°±0.3, 15.7°±0.3, 16.0°±0.3, and 19.9°±0.3. In some embodiments, the solid form exhibits at least two X-ray powder diffraction reflections selected from 3.2°±0.3, 3.3°±0.3, 4.6°±0.3, 6.8°±0.3, 7.1°±0.3, 8.0°±0.3, 12.5°±0.3, 15.7°±0.3, 16.0°±0.3, and 19.9°±0.3. In some embodiments, the solid form exhibits at least three X-ray powder diffraction reflections selected from 3.2°±0.3, 3.3°±0.3, 4.6°±0.3, 6.8°±0.3, 7.1°±0.3, 8.0°±0.3, 12.5°±0.3, 15.7°±0.3, 16.0°±0.3, and 19.9°±0.3. In some embodiments, the solid form exhibits at least four X-ray powder diffraction reflections selected from 3.2°±0.3, 3.3°±0.3, 4.6°±0.3, 6.8°±0.3, 7.1°±0.3, 8.0°±0.3, 12.5°±0.3, 15.7°±0.3, 16.0°±0.3, and 19.9°±0.3. In some embodiments, the solid form exhibits at least five X-ray powder diffraction reflections selected from 3.2°±0.3, 3.3°±0.3, 4.6°±0.3, 6.8°±0.3, 7.1°±0.3, 8.0°±0.3, 12.5°±0.3, 15.7°±0.3, 16.0°±0.3, and 19.9°±0.3. In some embodiments, the solid form exhibits at least six X-ray powder diffraction reflections selected from 3.2°±0.3, 3.3°±0.3, 4.6°±0.3, 6.8°±0.3, 7.1°±0.3, 8.0°±0.3, 12.5°±0.3, 15.7°±0.3, 16.0°±0.3, and 19.9°±0.3. In certain embodiments, the margin of error for any one of the reflections of Compound 6 is selected from ±0.5; ±0.4; ±0.3; ±0.2; ±0.1; and ±0.05. In some embodiments, Compound 6 Form I exhibits at least one of the X-ray powder diffraction pattern reflections in Table 6.

TABLE 6

Peak listing for the X-ray powder diffractogram of the crystalline solid state form of Compound 6 Form I.

| 2-Theta | d(Å) | Relative Intensity % |
|---|---|---|
| 3.167 | 27.87406 | 100 |
| 3.308 | 26.6838 | 97.1 |
| 4.576 | 19.29642 | 88.2 |
| 6.82 | 12.95005 | 90.8 |
| 7.116 | 12.41181 | 74.2 |
| 7.967 | 11.08828 | 44.1 |
| 12.471 | 7.09177 | 21.5 |
| 14.419 | 6.1379 | 17.5 |
| 15.725 | 5.63095 | 28.1 |
| 16.004 | 5.53334 | 23 |
| 17.349 | 5.10745 | 17.6 |
| 17.869 | 4.96005 | 15.5 |
| 18.55 | 4.77937 | 17.2 |
| 18.957 | 4.67762 | 17.3 |
| 19.898 | 4.45841 | 23.2 |
| 20.158 | 4.4016 | 17.9 |
| 21.698 | 4.09255 | 16.2 |
| 21.821 | 4.06979 | 17.7 |
| 25.764 | 3.45518 | 13.2 |
| 28.243 | 3.15721 | 9 |

In some embodiments, provided herein is a composition wherein the crystalline solid state form of Compound 6 Form I is substantially free of other crystalline or amorphous forms. In some embodiments, the amount of other crystalline or amorphous forms is 20% (w/w) or less. In some embodiments, the amount of other crystalline or amorphous forms is 15% (w/w) or less. In some embodiments, the amount of other crystalline or amorphous forms is 10% (w/w) or less. In some embodiments, the amount of other crystalline or amorphous forms is 5% (w/w) or less. In some embodiments, the amount of other crystalline or amorphous forms is 1% (w/w) or less.

Compound 6—Form II Crystalized with Isopropanol

In some embodiments, the present invention provides a crystalline solid state form of Compound 6 Form II, which is crystalized in the presence of acetonitrile. In some embodiments, the present invention provides a crystalline solid state form of Compound 6 Form II. In some embodiments, the solid form exhibits an X-ray powder diffraction reflection at a 2-theta value of 7.2°±0.3. In some embodiments, the solid form exhibits an X-ray powder diffraction reflection at a 2-theta value of 14.5°±0.3 and 16.1°±0.3. In some embodiments, the solid form exhibits an X-ray powder diffraction reflection at a 2-theta value of 15.8°±0.3 and 19.9°±0.3. In some embodiments, the solid form exhibits an X-ray powder diffraction reflection at a 2-theta value of 9.5°±0.3, 19.1°±0.3, 19.3°±0.3, and 21.9°±0.3.

In some embodiments, the solid form exhibits at least one X-ray powder diffraction reflection selected from 7.2°±0.3, 9.5°±0.3, 14.5°±0.3, 15.8°±0.3, 16.1°±0.3, 19.1°±0.3, 19.3°±0.3, 19.9°±0.3, and 21.9°±0.3. In some embodiments, the solid form exhibits at least two X-ray powder diffraction reflections selected from 7.2°±0.3, 9.5°±0.3, 14.5°±0.3, 15.8°±0.3, 16.1°±0.3, 19.1°±0.3, 19.3°±0.3, 19.9°±0.3, and 21.9°±0.3. In some embodiments, the solid form exhibits at least three X-ray powder diffraction reflections selected from 7.2°±0.3, 9.5°±0.3, 14.5°±0.3, 15.8°±0.3, 16.1°±0.3, 19.1°±0.3, 19.3°±0.3, 19.9°±0.3, and 21.9°±0.3. In some embodiments, the solid form exhibits at least four X-ray powder diffraction reflections selected from 7.2°±0.3, 9.5°±0.3, 14.5°±0.3, 15.8°±0.3, 16.1°±0.3, 19.1°±0.3, 19.3°±0.3, 19.9°±0.3, and 21.9°±0.3. In some embodiments, the solid form exhibits at least five X-ray powder diffraction reflections selected from 7.2°±0.3, 9.5°±0.3, 14.5°±0.3, 15.8°±0.3, 16.1°±0.3, 19.1°±0.3, 19.3°±0.3, 19.9°±0.3, and 21.9°±0.3. In some embodiments, the solid form exhibits at least six X-ray powder diffraction reflections selected from 7.2°±0.3, 9.5°±0.3, 14.5°±0.3, 15.8°±0.3, 16.1°±0.3, 19.1°±0.3, 19.3°±0.3, 19.9°±0.3, and 21.90°±0.3. In certain embodiments, the margin of error for any one of the reflections of Compound 6 is selected from +0.5; ±0.4; ±0.3; ±0.2; ±0.1; and ±0.05. In some embodiments, Compound 6 Form II exhibits at least one of the X-ray powder diffraction pattern reflections in Table 7.

TABLE 7

Peak listing for the X-ray powder diffractogram of the crystalline solid state form of Compound 6 Form II.

| 2-Theta | d(Å) | Relative Intensity % |
|---|---|---|
| 7.192 | 12.28074 | 100 |
| 9.548 | 9.25602 | 24.9 |
| 12.963 | 6.82373 | 18.2 |
| 14.542 | 6.08634 | 28 |
| 15.752 | 5.62148 | 64.2 |
| 16.093 | 5.50322 | 35.1 |
| 17.93 | 4.94318 | 16.6 |
| 18.579 | 4.77192 | 18.4 |
| 19.069 | 4.65039 | 19 |
| 19.267 | 4.60315 | 20.8 |
| 19.876 | 4.46329 | 44.5 |

TABLE 7-continued

Peak listing for the X-ray powder diffractogram of the crystalline solid state form of Compound 6 Form II.

| 2-Theta | d(Å) | Relative Intensity % |
|---|---|---|
| 21.059 | 4.21515 | 18.3 |
| 21.671 | 4.09752 | 18.2 |
| 21.908 | 4.05384 | 21.2 |
| 25.865 | 3.44185 | 14.8 |
| 26.28 | 3.38845 | 14.2 |
| 29.913 | 2.98465 | 14.7 |

In some embodiments, provided herein is a composition wherein the crystalline solid state form of Compound 6 Form II is substantially free of other crystalline or amorphous forms. In some embodiments, the amount of other crystalline or amorphous forms is 20% (w/w) or less. In some embodiments, the amount of other crystalline or amorphous forms is 15% (w/w) or less. In some embodiments, the amount of other crystalline or amorphous forms is 10% (w/w) or less. In some embodiments, the amount of other crystalline or amorphous forms is 5% (w/w) or less. In some embodiments, the amount of other crystalline or amorphous forms is 1% (w/w) or less.

Pharmaceutical Compositions

In certain embodiments, Compound 1, Compound 2, Compound 3, Compound 4, Compound 5, or Compound 6 is administered as a pure chemical. In other embodiments, Compound 1, Compound 2, Compound 3, Compound 4, Compound 5, or Compound 6, is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, $21^{st}$ Ed. Mack Pub. Co., Easton, PA (2005)).

Provided herein is a pharmaceutical composition comprising at least one of Compound 1, Compound 2, Compound 3, Compound 4, Compound 5, or Compound 6, together with one or more pharmaceutically acceptable carriers. The carrier(s) (or excipient(s)) is acceptable or suitable if the carrier is compatible with the other ingredients of the composition and not deleterious to the recipient (i.e., the subject or the patient) of the composition.

One embodiment provides a pharmaceutical composition comprising a pharmaceutically acceptable excipient and Compound 1, Compound 2, Compound 3, Compound 4, Compound 5, or Compound 6.

One embodiment provides a method of preparing a pharmaceutical composition comprising mixing Compound 1, Compound 2, Compound 3, Compound 4, Compound 5, or Compound 6, and a pharmaceutically acceptable carrier.

In certain embodiments, Compound 1, Compound 2, Compound 3, Compound 4, Compound 5, or Compound 6, is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, $21^{st}$ Ed. Mack Pub. Co., Easton, PA (2005)).

In some embodiments, the formulation comprises a Compound 1, Compound 2, Compound 3, Compound 4, Compound 5, or Compound 6; a pharmaceutically acceptable carrier; and a disintegrating agent. In some embodiments, the disintegrating agent is selected from the group consisting of natural starch, a pregelatinized starch, a sodium starch, methylcrystalline cellulose, methylcellulose, croscarmellose, croscarmellose sodium, cross-linked sodium carboxymethylcellulose, cross-linked carboxymethylcellulose, cross-linked croscarmellose, cross-linked starch such as sodium starch glycolate, cross-linked polymer such as crospovidone, cross-linked polyvinylpyrrolidone, sodium alginate, a clay, or a gum. In some embodiments, the disintegrating agent is croscarmellose sodium.

In some embodiments, Compound 1, Compound 2, Compound 3, Compound 4, Compound 5, or Compound 6, is formulated for administration by injection. In some instances, the injection formulation is an aqueous formulation. In some instances, the injection formulation is a non-aqueous formulation. In some instances, the injection formulation is an oil-based formulation, such as sesame oil, or the like.

The dose of the composition comprising Compound 1, Compound 2, Compound 3, Compound 4, Compound 5, or Compound 6, differs depending upon the subject or patient's (e.g., human) condition. In some embodiments, such factors include general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

Methods of Treatment

One embodiment provides Compound 1, Compound 2, Compound 3, Compound 4, Compound 5, or Compound 6, for use in a method of treatment of the human or animal body.

One embodiment provides Compound 1, Compound 2, Compound 3, Compound 4, Compound 5, or Compound 6, for use in a method of treatment of cancer or neoplastic disease.

One embodiment provides a use of Compound 1, Compound 2, Compound 3, Compound 4, Compound 5, or Compound 6, in the manufacture of a medicament for the treatment of cancer or neoplastic disease.

In some embodiments, described herein is a method of treating cancer in a patient in need thereof comprising administering to the patient Compound 1, Compound 2, Compound 3, Compound 4, Compound 5, or Compound 6.

In some embodiments, described herein is a method of treating cancer in a patient in need thereof comprising administering to the patient a pharmaceutical composition comprising Compound 1, Compound 2, Compound 3, Compound 4, Compound 5, or Compound 6, and a pharmaceutically acceptable excipient.

Provided herein is the method wherein the pharmaceutical composition is administered orally. Provided herein is the method wherein the pharmaceutical composition is administered by injection.

Other embodiments and uses will be apparent to one skilled in the art in light of the present disclosures. The following examples are provided merely as illustrative of various embodiments and shall not be construed to limit the invention in any way.

EXAMPLES

The present disclosure is further illustrated by the following examples, which should not be construed as limiting in any way. The experimental procedures to generate the data shown are discussed in more detail below. The disclosure has been described in an illustrative manner, and it is to be understood that the terminology used is intended to be in the nature of description rather than of limitation.

General Experimental, Instrument, and Methodology Details

A general synthesis for (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide is described in paragraphs in PCT/US2020/057132.

X-Ray Powder Diffraction (XRPD)

For XRPD analysis, a Bruker D8 Advance X-ray powder diffractometer was used equipped with a LynxEye detector. The XRPD parameters used are listed in Table 8.

TABLE 8

| Parameters for XRPD experiments | |
|---|---|
| Instrument | Bruker, D8 Advance |
| Radiation | Cu Kα (λ = 1.5418 Å) |
| Detector | LynxEye |
| Scan angle | 3-40° (2θ) |
| Scan step | 0.02° (2θ) |
| Scan speed | 0.2 s/step |
| Tube voltage/current | 40 kV/40 mA |
| Divergence slit | 0.6 mm |
| Rotation | On |
| Sample holder | Zero-background sample pan |

Differential Scanning Calorimetry (DSC)

DSC was performed using a Discovery DSC 250 (TA Instruments, US). The sample was placed into an aluminum pin-hole hermetic pan and the weight was accurately recorded. The sample was heated at a rate of 10° C./min from 25° C. to the final temperature. The DSC parameters used are listed in Table 9.

TABLE 9

| Parameters for DSC experiments | |
|---|---|
| Instrument | TA, Discovery DSC 250 |
| Sample pan | Aluminum, pin-holed |
| Temperature range | 25-300° C. |
| Heating rate | 10° C./min |

TABLE 9-continued

| Parameters for DSC experiments | |
|---|---|
| Purge gas | N2 |
| Flow rate | 50 mL/min |

Thermo-Gravimetric Analysis (TGA)

TGA was carried out on a Discovery TGA 55 (TA Instruments, US). The sample was placed into an open tared aluminum pan, automatically weighed, and inserted into the TGA furnace. The sample was heated at a rate of 10° C./min from ambient temperature to the final temperature. The TGA parameters used are listed in Table 10.

TABLE 10

| Parameters for TGA experiments | |
|---|---|
| Instrument | TA, Discovery TGA 55 |
| Sample pan | Aluminum, open |
| Temperature range | RT-300° C. |
| Heating rate | 10° C./min |
| Purge gas | N2 |
| Flow rate | Balance chamber: 40 mL/min<br>Sample chamber: 25 mL/min |

Dynamic Vapor Sorption (DVS)

Moisture sorption/desorption data was collected on a DVS Intrinsic PLUS (SMS, UK). The sample was placed into a tared sample chamber and automatically weighed. The sample was dried at 40° C./0%0 RH until the dm/dt was less than 0.00200 and cooled to 25° C. The DVS parameters used are listed in Table 11.

TABLE 11

| Parameters for DVS experiments | |
|---|---|
| Instrument | SMS, DVS Intrinsic PLUS |
| dm/dt | 0.002%/min |
| Drying/Measurement temperature | 40° C./25° C. |
| Cycle | Full cycle |
| Save data rate | 5 s |
| Total flow rate | 200 ccm |
| Post experiment total flow | 200 ccm |
| Minimum time per step | 30 min |
| Maximum time per step | 120 min |
| Method | Adsorption: 0, 10, 20, 30, 40, 50, 60, 70, 80, 90<br>Desorption: 80, 70, 60, 50, 40, 30, 20, 10, 0 |

Polarized Light Microscopy (PLM)

Light microscopy was performed using a Polarizing Microscope ECLIPSE LV 100POL (Nikon, JPN).

Proton Nuclear Magnetic Resonance (1H-NMR)

$^1$H-NMR was performed using Bruker Advance 300 equipped with automated sampler (B-ACS 120).

Ultra Performance Liquid Chromatography (UPLC) Method

UPLC method for solubility and stability testing is listed in Table 12.

TABLE 12

| Parameters for UPLC experiments | |
|---|---|
| Instrument | Acquity UPLC |
| Column | Acquity UPLC @ BEH C18, 2.1*50 mm, 1.7 μm |
| Column temperature | 40° C. |
| Mobile phase | A: 0.1% TFA in H2O<br>B: 0.1% TFA in ACN |

TABLE 12-continued

| Parameters for UPLC experiments | | | |
|---|---|---|---|
| Flow rate | 0.5 mL/min | | |
| Injection volume | 2 μL | | |
| Wavelength | DAD; 248 nm | | |
| Run time | 6.0 min | | |
| Post time | 1.0 min | | |
| Diluent | ACN/water (1:1) | | |
| Gradient | Time (min) | % A | % B |
| | 0.0 | 80 | 20 |
| | 3.0 | 55 | 45 |
| | 6.0 | 0 | 100 |
| | 7.0 | 80 | 20 |

Example 1: Characterization of (S)—N-(3-(2-(((R)-1-hydroxypropan-2-yl)amino)-6-morpholinopyridin-4-yl)-4-methyl phenyl)-3-(2,2,2-trifluoroethyl)pyrrolidine-1-carboxamide (Compound 1)

Figure 11:
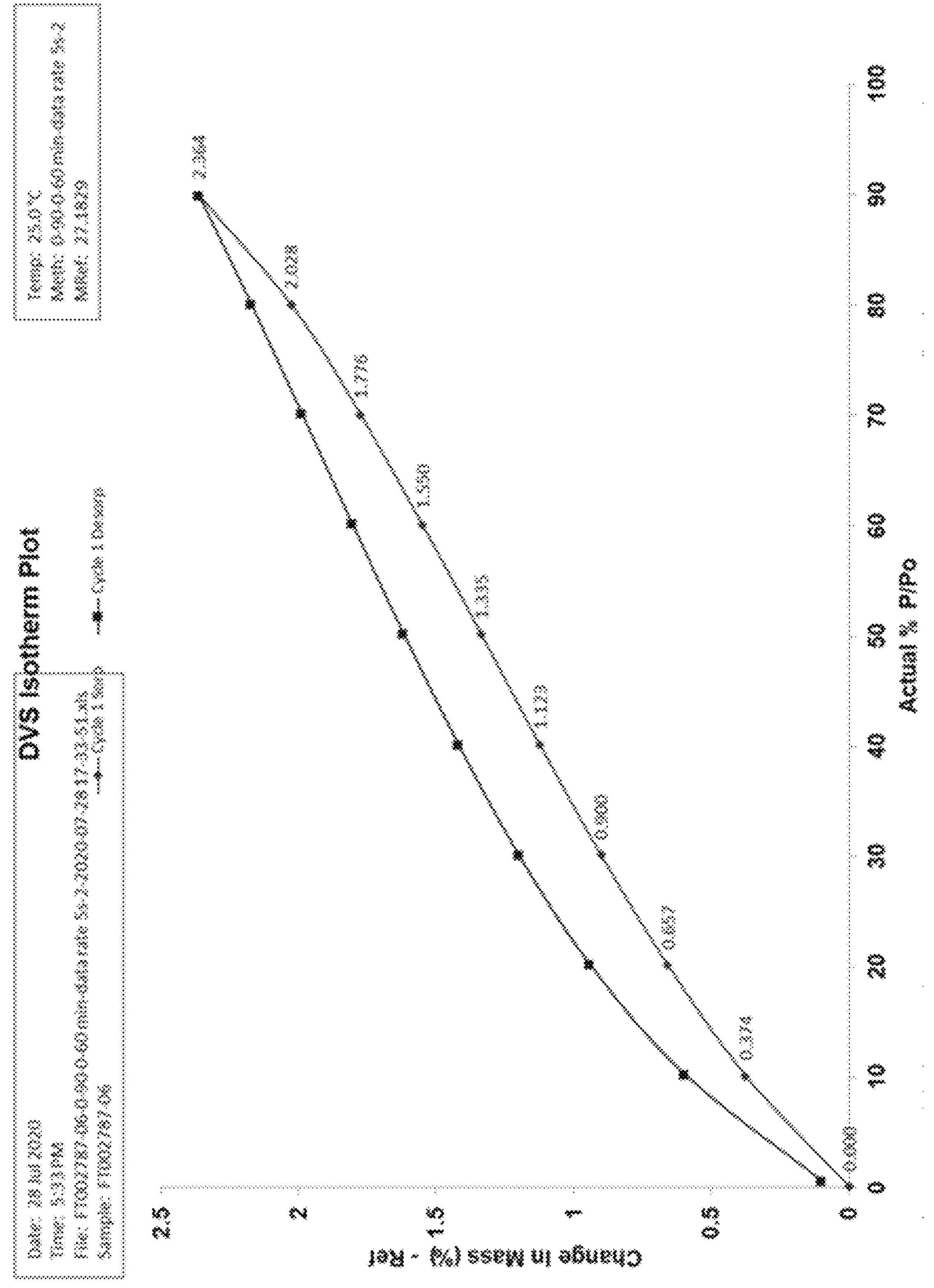
FIG. 11 shows the Dynamic Vapor Sorption of Compound 1.

The amorphous form Compound 1 was identified by XRPD as shown in FIG. 1. Thermograms in FIG. 2 showed that the sample had −1.8% weight loss at RT—150° C. and an broad endothermic peak at 97.2° C.±5.0. The amorphous material was slightly hygroscopic with 2% water uptake at 80% RH (FIG. 11). The material remained amorphous after DVS testing.

Compound 1 is insoluble in n-heptane and water (<1 mg/mL) and soluble (>100 mg/mL) in methanol, ethanol, acetone, tetrahydrofuran, methyl ethyl ketone, ethyl acetate, acetonitrile, isobutanol, isopropyl alcohol and isopropyl acetate. Compound 1 has a solubility of about 60 mg/mL in methyl t-butyl ether.

Example 2: Characterization of (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide hydrochloride (Compound 2)

Figure 3:
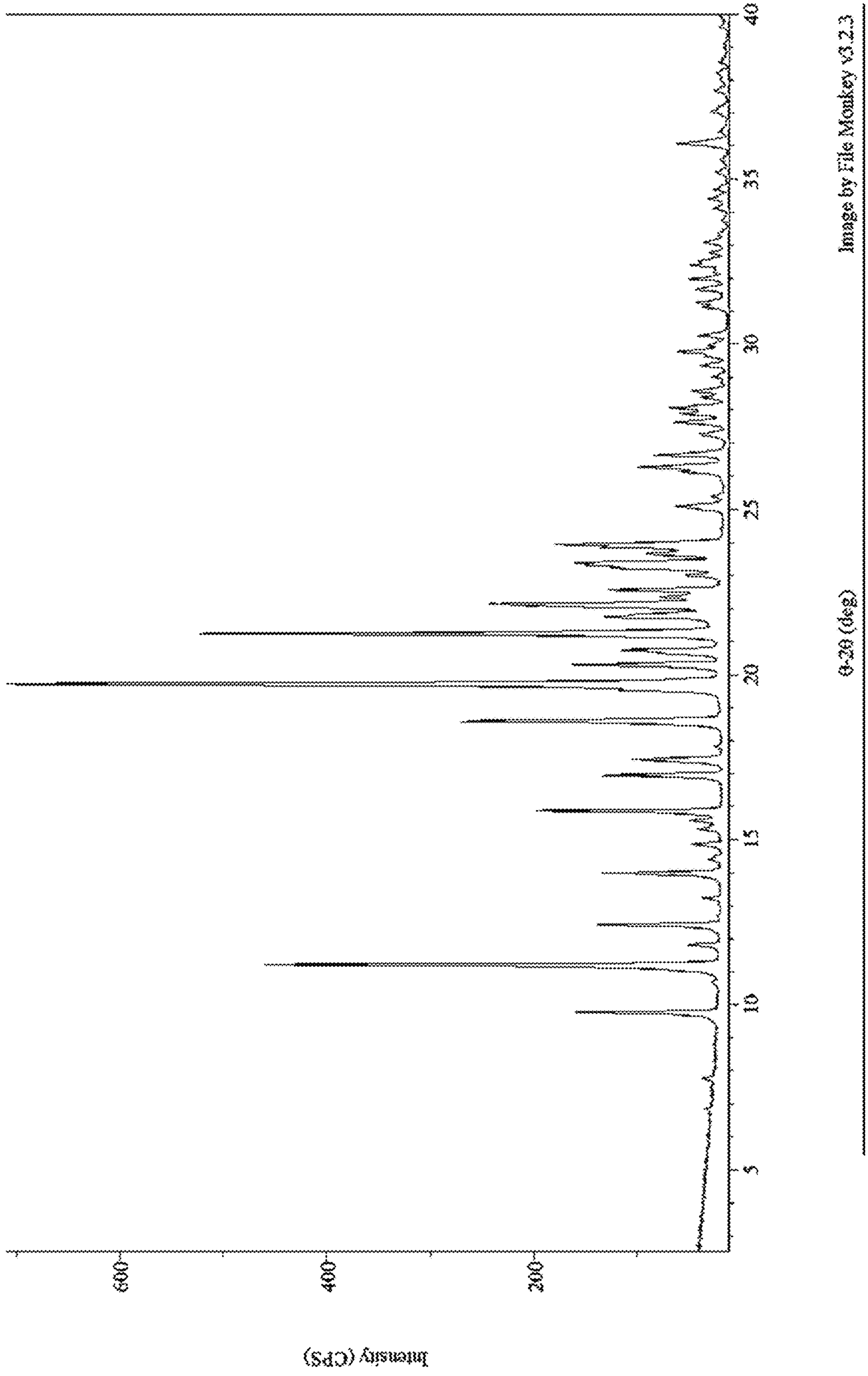
FIG. 3 shows an X-ray diffraction pattern of crystalline Compound 2.
Figure 12:
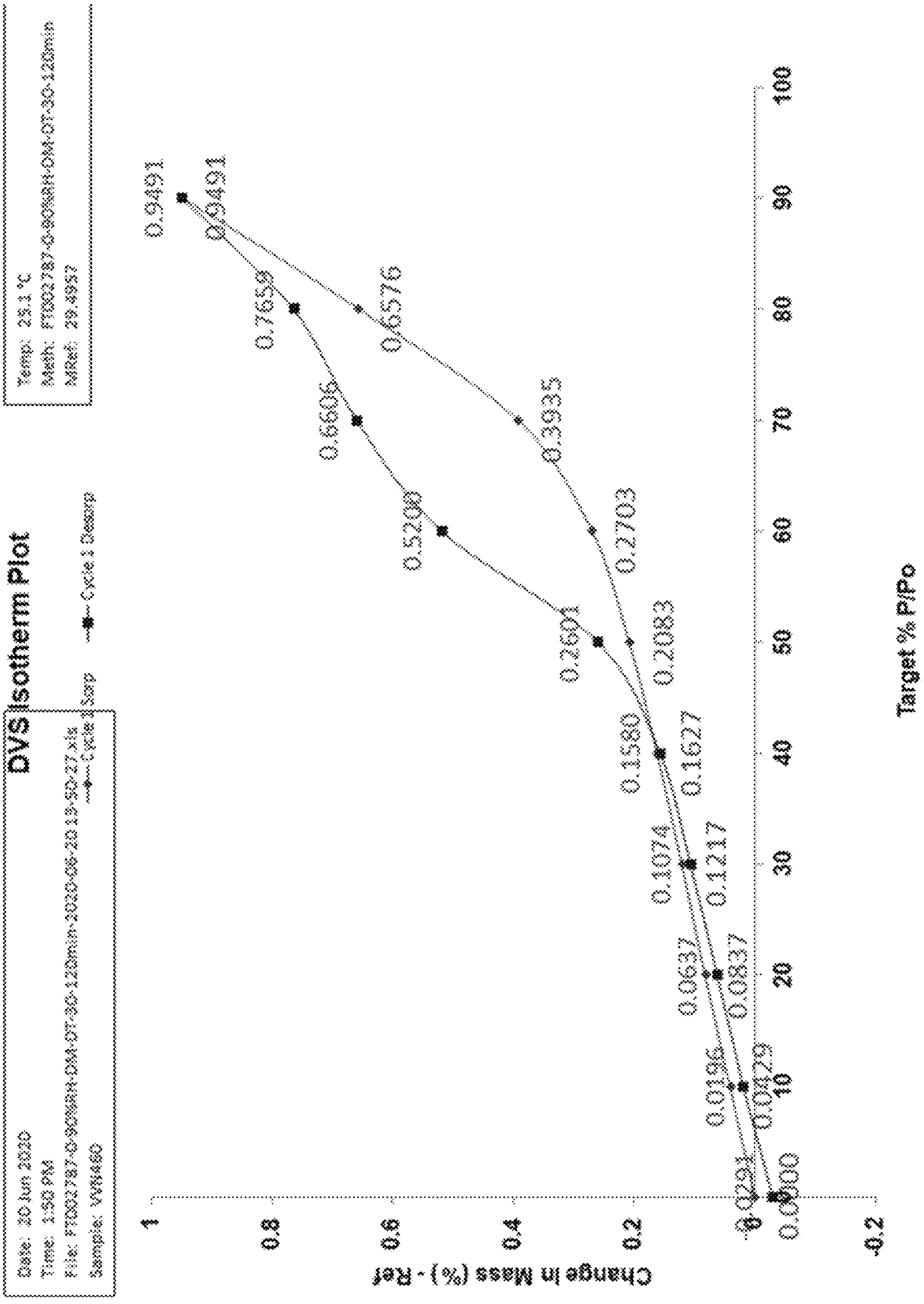
FIG. 12 shows the Dynamic Vapor Sorption of Compound 2.

About 390 mg of Compound 1 was added into 10V of acetone at RT to obtain a clear solution. Then, 69.3 μL of concentrated HCl (1.1 eq.) was added and precipitation occurred after 1 min. The resulting suspension was held at RT for 3 hours. Solids were collected by filtration and dried under vacuum at 50° C. overnight. Compound 2 was obtained as an off-white solid with the yield of ~81%. Compound 2 was highly crystalline as shown in FIG. 3. Compound 2 was slightly hydroscopic with 0.66% water uptake at 80% relative humidity and 0.95% at 90% relative humidity as determined by DVS (FIG. 12). Compound 2 exhibited a DSC peak at 229.94° C.±5.0 and a weight loss of less than 1.0%±5.0 up to 160° C.±10.0 as determined by TGA (FIG. 4).

An amorphous solid state form of (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide hydrochloride is attainable. However, unless specifically denoted as amorphous, "Compound 2" refers to the crystalline form shown in FIG. 3. Amorphous (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide hydrochloride was formed by rapid evaporation of 15 mg of Compound 2 dissolved in 0.5 mL of methanol. The solid was confirmed to be amorphous by XRPD. Slurry of amorphous (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide hydrochloride in 0.5 mL of the solvents in Table 13 were prepared. Each suspension was stirred for one day at 50° C. and at RT. Each suspension was filtered and analyzed by XRPD. In each experiment, conversion from amorphous (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide hydrochloride to crystalline Compound 2 was observed.

TABLE 13

Summary of Slurry Experiments

| Solvent | Temperature | Resulting Solid State Form |
|---|---|---|
| Ethanol | RT | Form I |
| Acetone | | Form I |
| n-Heptane | | Form I |
| Ethyl acetate | | Form I |
| Water | | Form I |
| Ethanol | 50° C. | Form I |
| Acetone | | Form I |
| n-Heptane | | Form I |
| Ethyl acetate | | Form I |
| Water | | Form I |

Compound 1 and Compound 2 were evaluated for stability at 60° C. and 40° C. at 75% relative humidity for 9 days. At 0, 3, and 9 days, the samples were dissolved with diluent to prepare a solution for purity analysis by UPLC. Solid samples were also analyzed by XRPD to check the crystal form. The results of the study are summarized below in Table 14.

TABLE 14

Summary of Stability Studies

| | | 40° C./75% RH | | | 60° C. | | |
|---|---|---|---|---|---|---|---|
| | Purity −0 d (Area %) | Purity −3 d | Purity −9 d | XRPD | Purity −3 d | Purity −9 d | XRPD |
| Compound 1 | 99.43 | 99.42 | 99.40 | No change | 99.39 | 99.42 | No change |
| Compound 2 | 99.77 | 99.74 | 99.76 | | 99.73 | 99.74 | |

A solution of Compound 2 was evaluated for stability in 0.5% MC/0.1% Tween 80 at 10 mg/mL. 10.7 mg of Compound 2 was weighed into a sample vial, and then 500 μL of 1% MC and 500 μL of 0.2% Tween 80 were added to obtain a suspension at 10 mg/mL (calculated as the free base). The mixture was kept stirring for 15 min at RT and the suspension was placed at RT for 7 days. No form change occurred, however purity decreased by 0.13% after 7 days as determined by UPLC.

Thermodynamic solubility of Compound 2 was measured in 13 solvents at RT and 50° C. by UPLC, respectively. The results are summarized in Table 15. Compound 2 showed the highest solubility in MeOH, at about 102 mg/mL at 50° C. and 55 mg/mL at RT. In most of other selected solvents, the compound was almost insoluble (<0.5 mg/mL) except in EtOH and water where it was slightly soluble (6-9 mg/mL). The solid forms of the residual solids from solubility testing were examined by XRPD and no form change occurred during the solubility testing.

TABLE 15

Summary of Solubility Experiments

| Solvent | Solubility at RT (mg/mL) | XRPD at 4 d | Solubility at 50° C.(mg/mL) | XRPD at 1 d |
|---|---|---|---|---|
| MeOH | 54.67 | Form I | 101.89 | Form I |
| EtOH | 7.15 | Form I | 8.82 | Form I |
| Acetone | 0.65 | Form I | 0.45 | Form I |
| MEK | 0.01 | Form I | 0.28 | Form I |
| Hept | 0.01 | Form I | 0.01 | Form I |
| IPA | 1.69 | Form I | 2.80 | Form I |
| EA | 0.06 | Form I | 0.09 | Form I |
| IPAC | 0.02 | Form I | 0.03 | Form I |
| MTBE | 0.02 | Form I | 0.01 | Form I |
| MIBK | 0.05 | Form I | 0.11 | Form I |
| ACN | 0.01 | Form I | 0.92 | Form I |
| Cyclohexane | 0.01 | Form I | 0.05 | Form I |
| Water | 6.15 | Form I | 6.73 | Form I |

Comparison dissolution trials were performed on Compounds 1 and 2. About 20 mg of each sample was weighed into a sample vial and then 4 mL of media was added to make a suspension. All suspensions were shaken at 37° C. with a rate of 200 rpm. At 0.5, 2 and 24 hours, each suspension was filtered, and the filtrate was analyzed by UPLC to test the solubility. He pH of the filtrate was measured, and the filter cake was analyzed by XRPD. Compound 1 has very low solubility in water (<9 μg/mL), while Compound 2 exhibits a solubility in water of about 2.5 mg/mL. In biorelevant dissolution media FaSSIF and FeSSIF, the solubility of the Compound 1 and Compound 2 were similar. Compound 1 converted to Compound 2 in FaSSGF. The experimental results are summarized in Table 16.

TABLE 13

Dissolution of Compound 1 and Compound 2

| | | Compound 1 | Compound 2 |
|---|---|---|---|
| Solubility (mg/mL) 0.5/2/24 h | Water | 0.004/0.004/0.009 (pH 6.4) | 1.42/1.36/2.49 (pH 3.1) |
| | SGF | 0.48/0.35/0.83 | 0.2/0.27/0.39 |
| | FeSSIF | 0.15/0.17/0.15 | 0.21/0.20/0.23 |
| | FaSSIF | 0.024/0.022/0.018 | 0.024/0.021/0.027 |

Example 3: Characterization of (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide hydrobromide (Compound 3)

Figure 5:
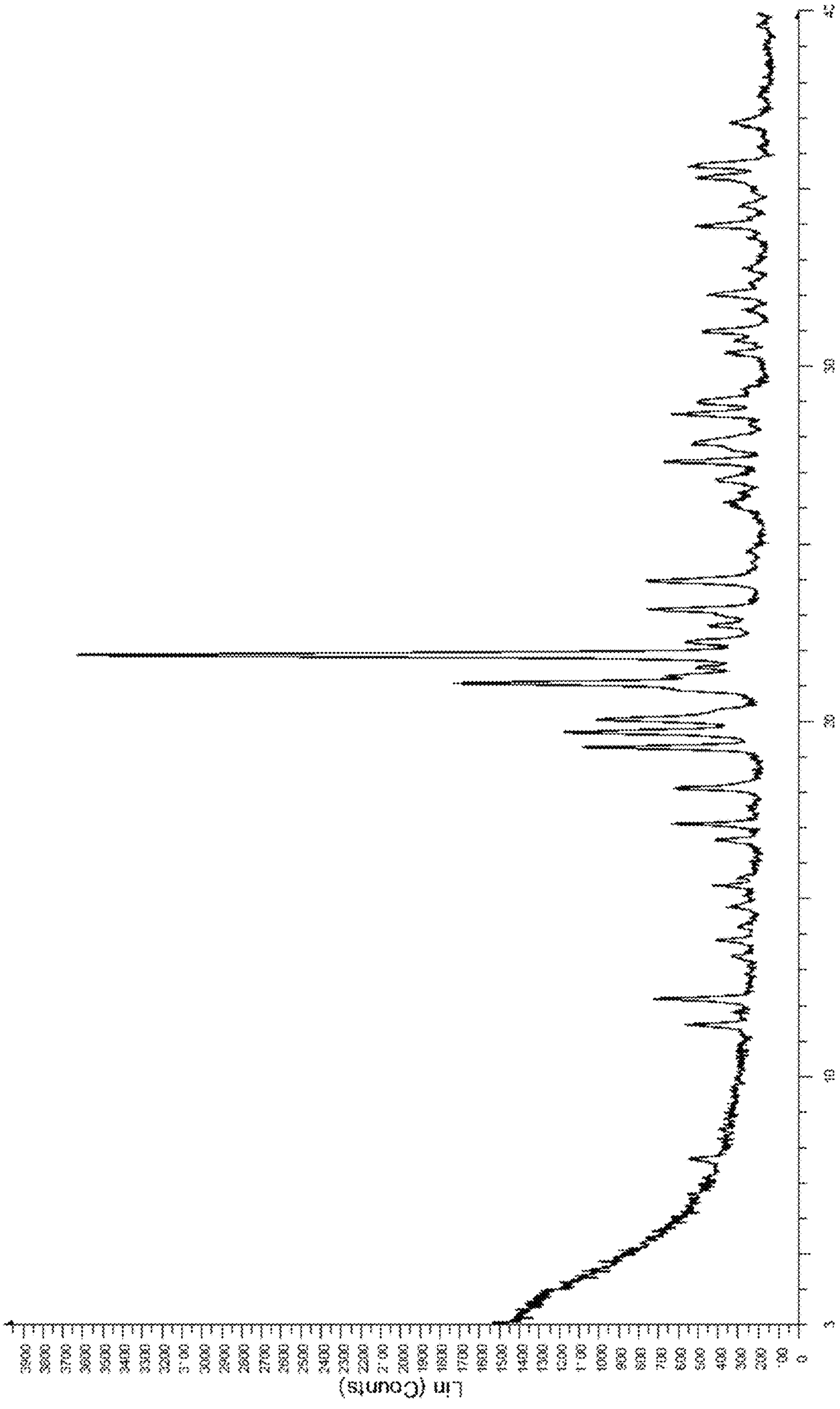
FIG. 5 shows an X-ray diffraction pattern of crystalline Compound 3.
Figure 13:
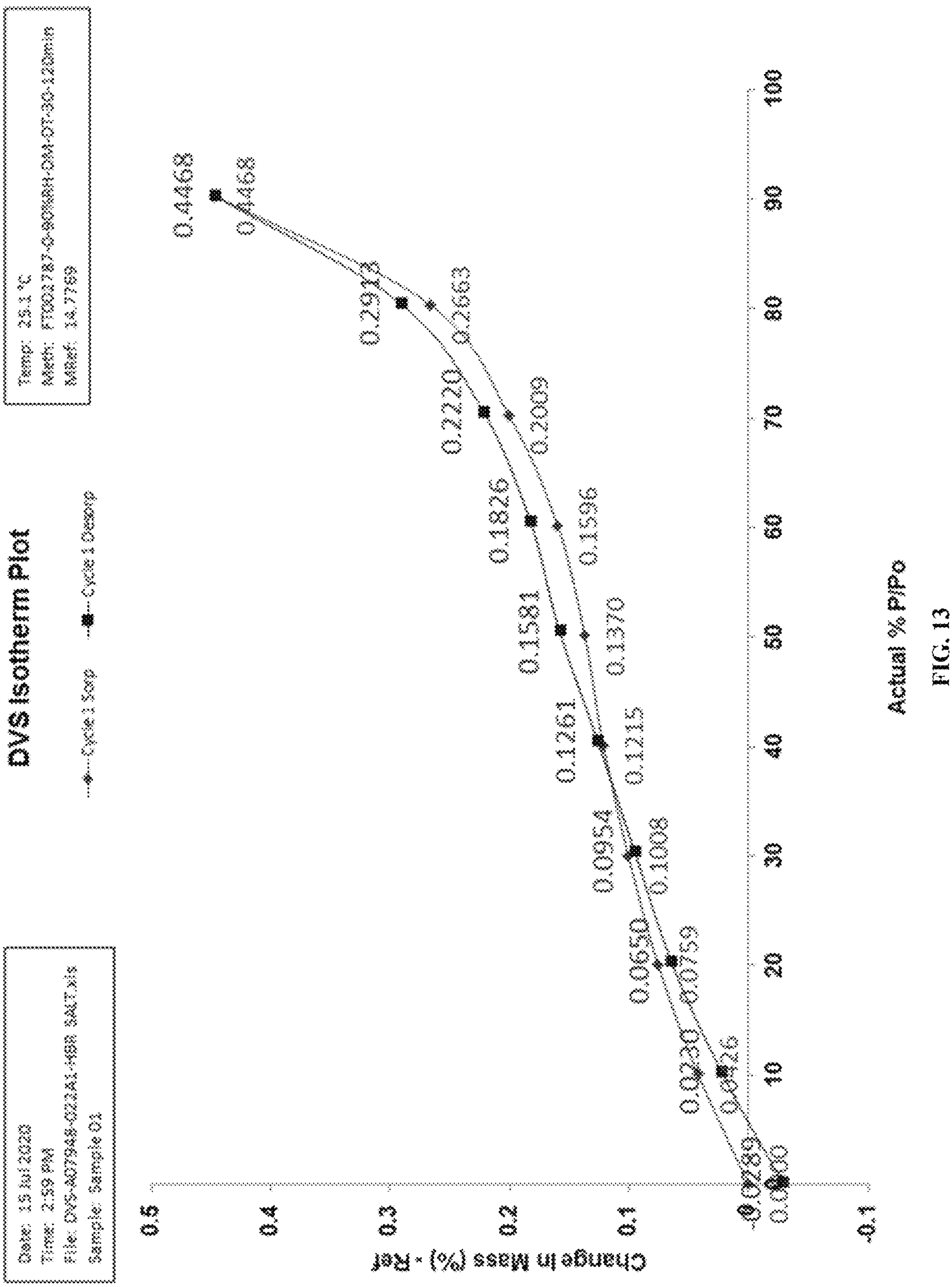
FIG. 13 shows Dynamic Vapor Sorption of Compound 3.

Compound 3 was synthesized by dissolving 26 mg of Compound 1 in acetone and adding 1 equivalent of hydrobromic acid at room temperature. Stirring for 30 mins yielded a slurry, the solid of which was isolated via filtration. The solid was highly crystalline as shown in FIG. 5. Compound 3 was slightly hydroscopic with 0.27% water uptake at 80% relative humidity and 0.45% at 90% relative humidity as determined by DVS (FIG. 13). Compound 3 exhibited a DSC peak at 222.2° C.±5.0 and a weight loss of less than 1.0%±0.5 up to 150° C. 10.0 as determined by TGA (FIG. 6).

Example 4: Characterization of (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide 4-methylbenzenesulfonate (Compound 4)

Figure 7:
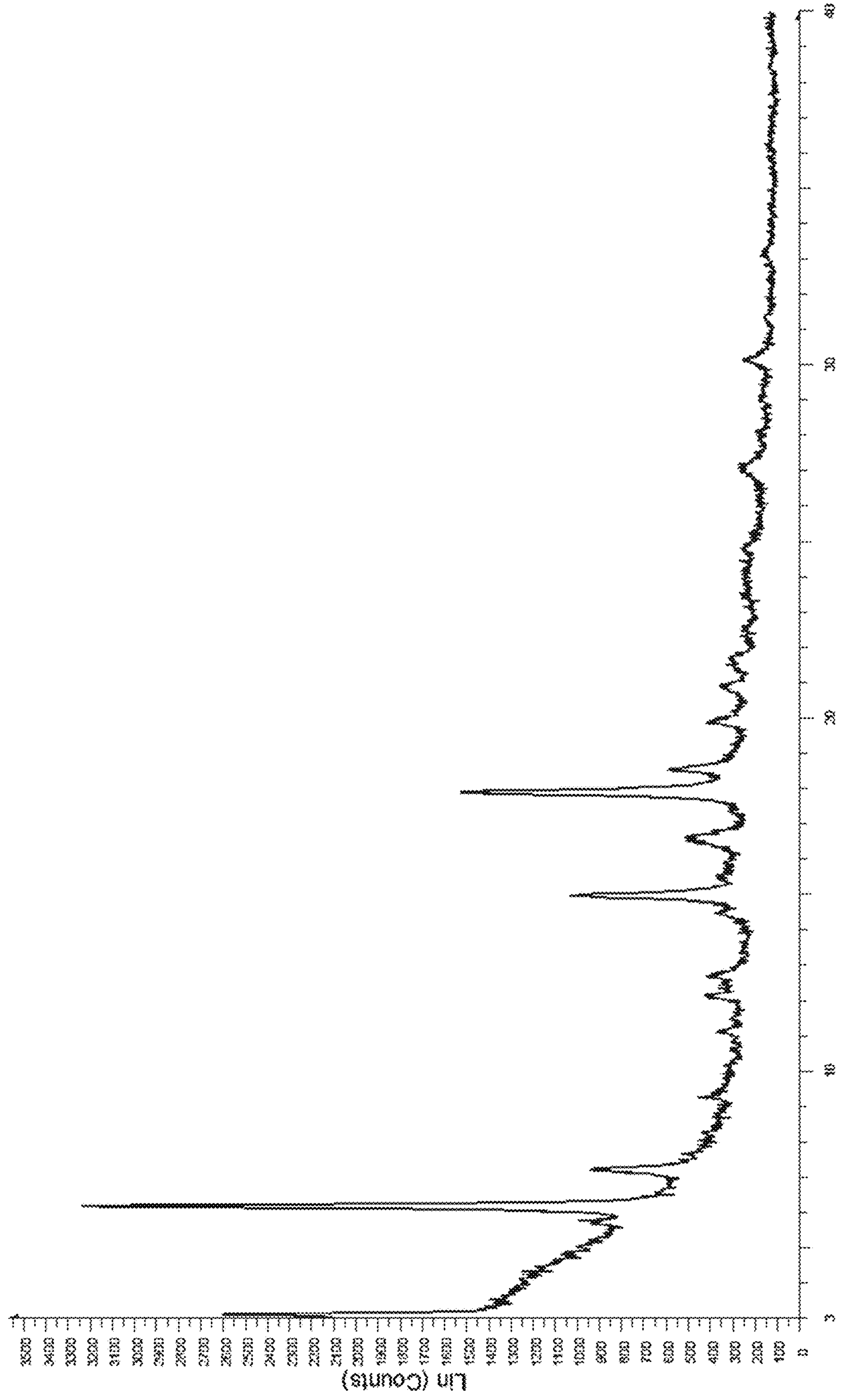
FIG. 7 shows an X-ray diffraction pattern of crystalline Compound 4 Form I crystalized from MTBE.
Figure 8:
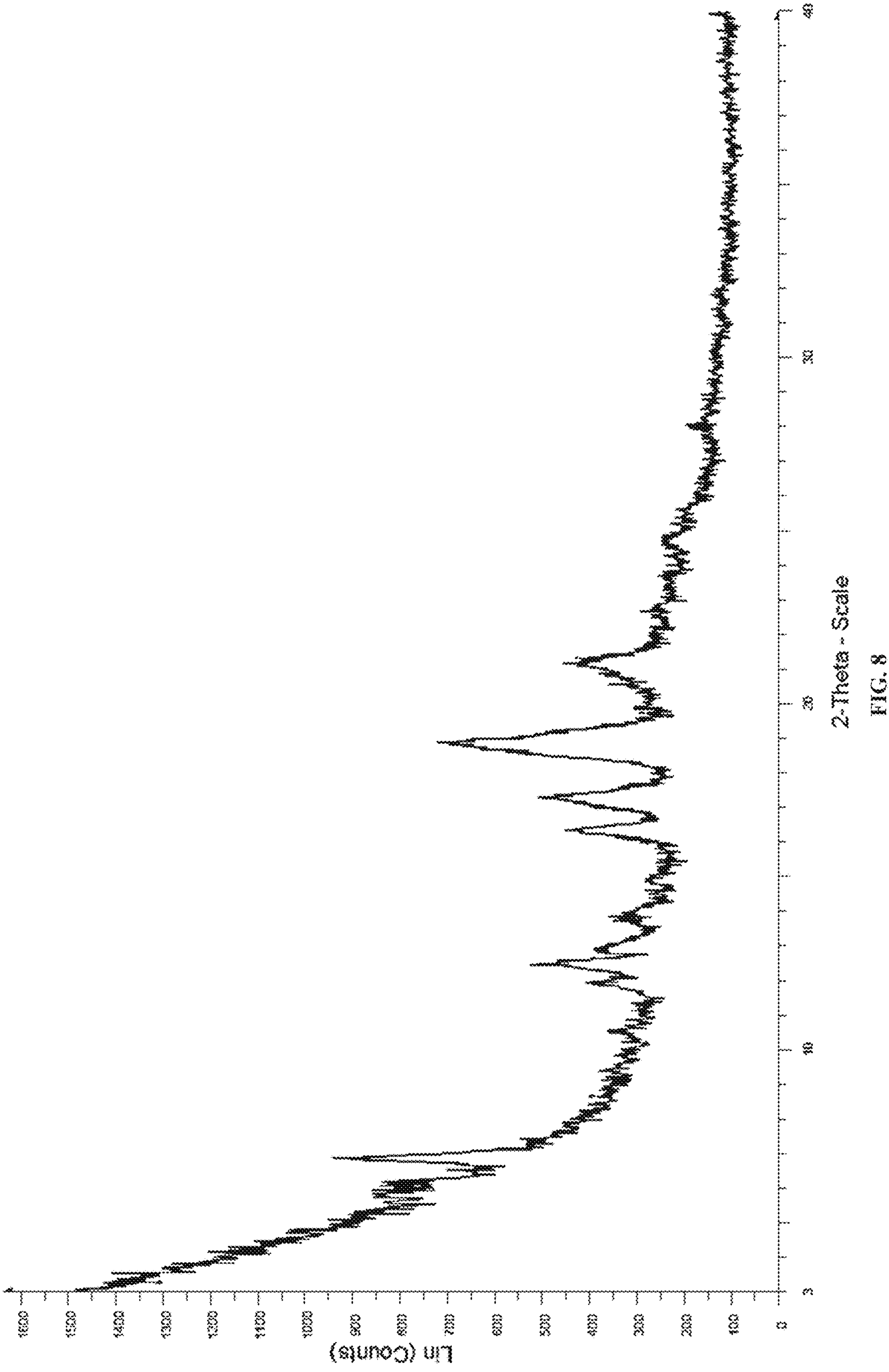
FIG. 8 shows an X-ray diffraction pattern of crystalline Compound 4 Form II crystalized from acetone.

Compound 4 was prepared by adding 1 equivalent of p-toluene sulfonic acid to Compound 1 in acetone or MTBE. In MTBE, the reagents were stirred for 1 hour at 50° C., after which solids appeared and were isolated by filtration to give crystalline Compound 4 Form I as shown in FIG. 7. In acetone, the reagents were stirred for 2 hours, after which solids appeared and were isolated by filtration to give crystalline Compound 4 Form II as shown in FIG. 8. An amorphous form of (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide 4-methylbenzenesulfonate was obtained when performing the synthesis in ethyl acetate and evaporating the solvent, as determined by XRPD.

Example 5: Characterization of (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide phosphate (Compound 5)

Figure 9:
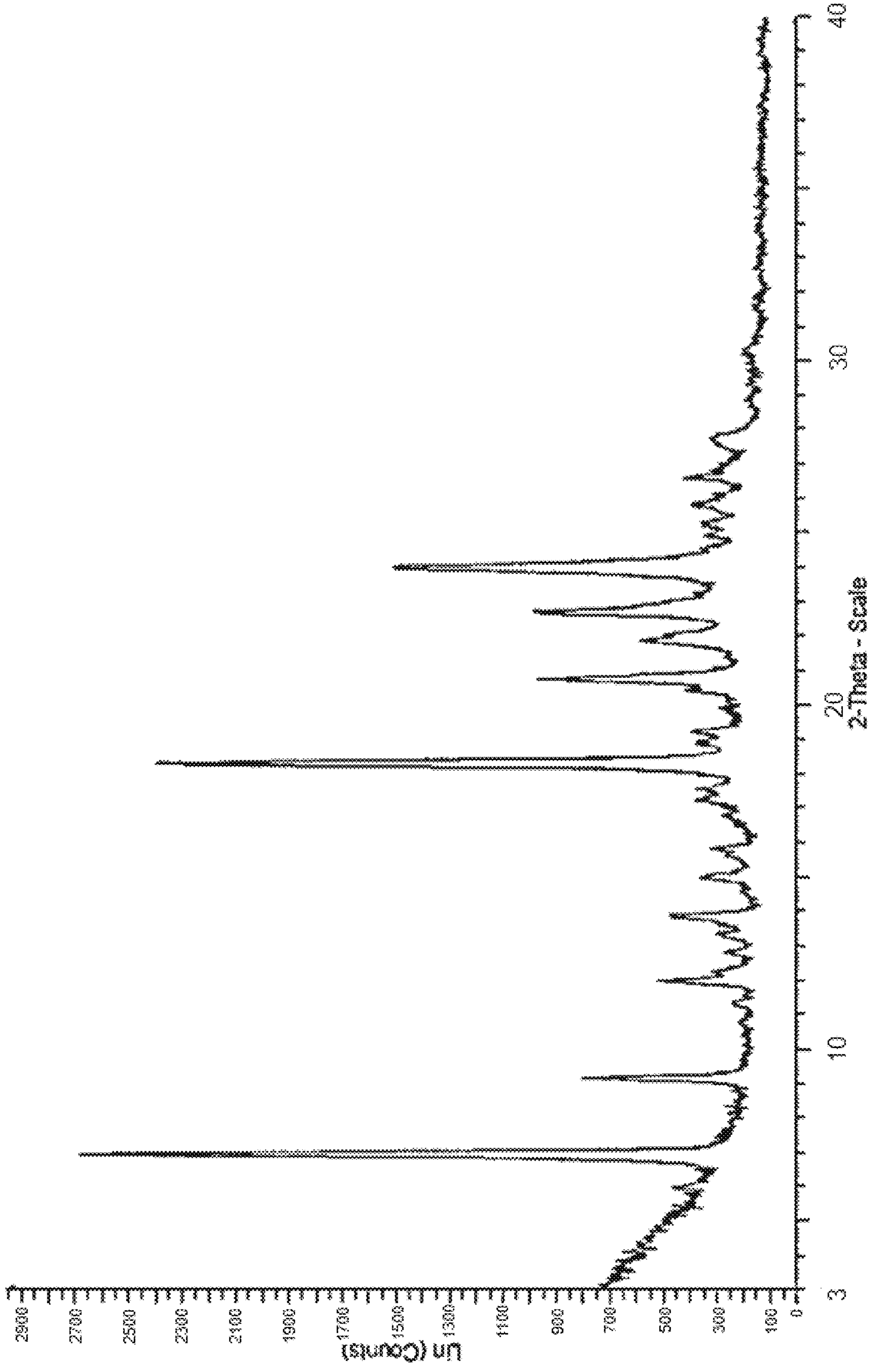
FIG. 9 shows an X-ray diffraction pattern of crystalline Compound 5.

Compound 5 was prepared by adding 1 equivalent of phosphoric acid to Compound 1 in methanol at room temperature. The reagents were stirred overnight, after which solids appeared and were isolated by filtration to give crystalline Compound 5 as shown in FIG. 9. Compound 5 exhibited a DSC desolvation/dehydration between 37-66° C.±5.0 and an endothermic melting point peak at 150.6° C.±5.0. A two step weight loss occurred about 3.3% 0.5 and 2.9%±0.5 occurred heating through 177° C.±10.0 as determined by TGA (FIG. 10). An amorphous form of (S)—N-(3-(2-(((R)-1-hydroxypropan-2-yl)amino)-6-morpholinopyridin-4-yl)-4-methylphenyl)-3-(2,2,2-trifluoroethyl) pyrrolidine-1-carboxamide phosphate was obtained when performing the synthesis in acetonitrile or ethyl acetate and evaporating the solvent, as determined by XRPD.

Example 6: Characterization of (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide sulfate (Compound 6)

Compound 6 was prepared by adding 1 equivalent of sulfuric acid to Compound 1 in acetonitrile or isopropyl alcohol. In acetonitrile, the reagents were combined and stirred resulting in the appearance of solids which were isolated by filtration to give crystalline Compound 6 Form I. In isopropyl alcohol, the reagents were combined and stirred resulting in the appearance of solids which were isolated by filtration to give crystalline Compound 6 Form II. An amorphous form of (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide sulfate was obtained when performing the reaction in acetone with 0.5 equivalents of sulfuric acid and evaporating the acetone, as determined by XRPD.

Example 7: Drug Product Formulation and Manufacturing Process

The formulation of the drug product provides an immediate release of Compound 2 over a period of approximately 1 hr. As the tablet is exposed to water and starts to disintegrate, drug substance is quickly released from the tablet core. The tablets are intended to dissolve completely in the stomach where the solubility is highest. In order to enable fast dissolution, a super-disintegrant such as croscarmellose sodium, is added to the formulation. Other components of the formulation include fillers such as microcrystalline cellulose, mannitol and hypromellose succinate acetate, anti-adherent such as talc, glidant such as silicon dioxide, and a lubricant such as sodium steryl fumarate. The tablets are film-coated using non-functional coatings containing polyvinyl alcohol, plasticizer such as PEG, titanium dioxide, and other coloring pigments.

Figure 14:
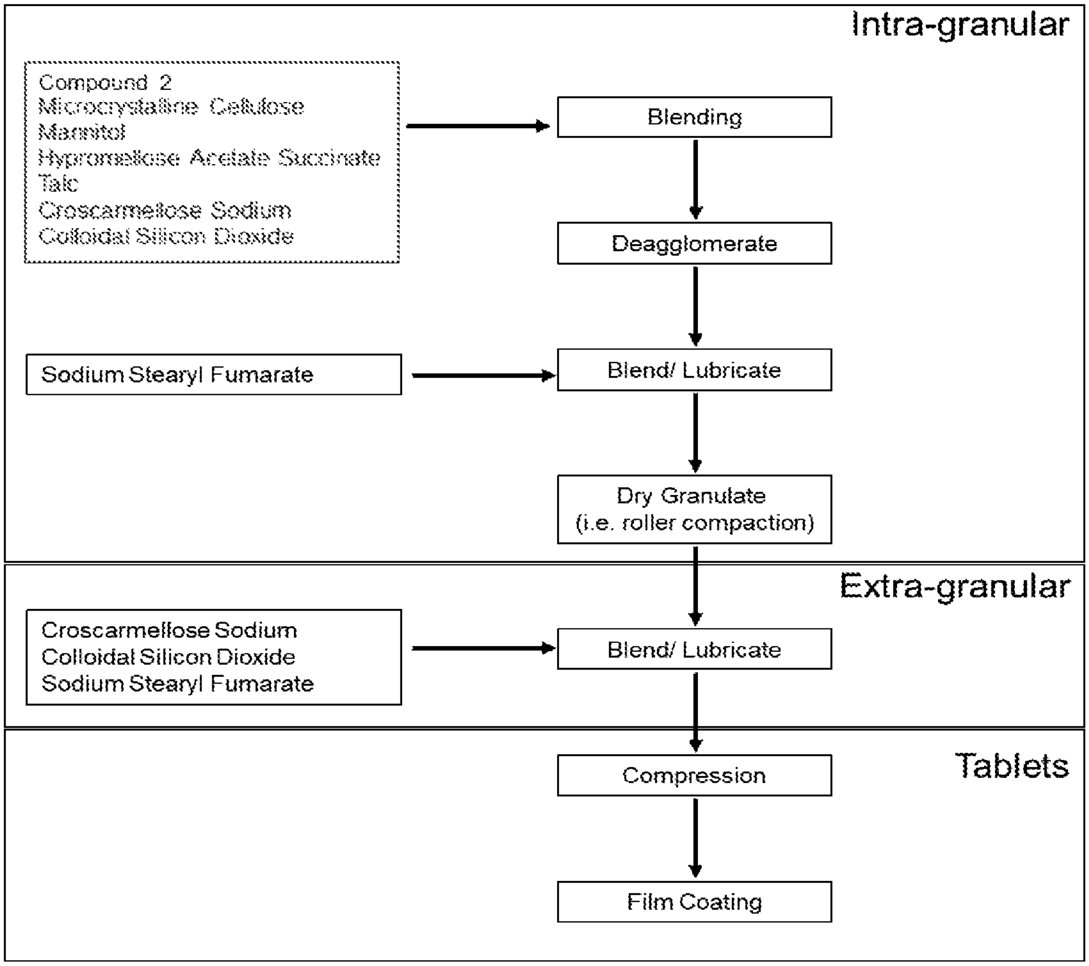
FIG. 14 shows an exemplary tablet manufacturing process.

FIG. 14 illustrates the manufacturing process used for an exemplary drug product. A dry granulation process was selected for the manufacture of tablets in order to improve blend flow in the tablet press and weight uniformity of the tablet core formulation. The tablet manufacturing process consists of first blending Compound 2, microcrystalline cellulose, mannitol, hypromellose succinate acetate, talc, croscarmellose sodium, and silicon dioxide in a blender. The blended material is passed through a Comil to breakup any aggregates, before adding sodium stearyl fumarate and blending further. The lubricated blend is dry granulated in a roller compactor to increase density of the material, followed by milling. To the granulated milled material, which represents about 97% of the formulation on a weight basis, are added croscarmellose sodium, silicon dioxide, and sodium stearyl fumarate. This mixture of granules and extra-granular excipients is blended to prepare the final composition for tableting. Tablet cores are compressed using a rotary tablet press. Different tablet strengths maybe created by adjusting tablet weights (e.g., 25 and 100 mg strength tablets). After compression, tablet cores are coated using an aqueous based film coating system in a pan coater.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A solid form of(S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide hydrochloride, depicted below as Compound 2, Compound 2

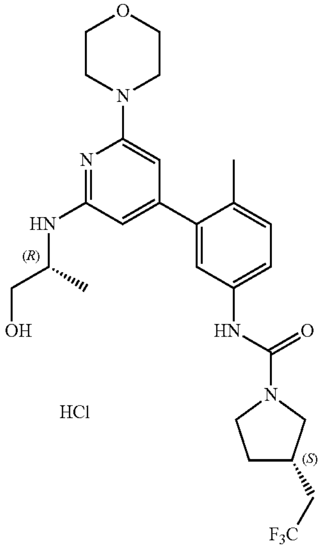

wherein the solid form is crystalline.

2. The solid form of claim 1, wherein the solid form exhibits an X-ray powder diffraction reflection at a 2-theta value of 19.7°±0.3.

3. The solid form of claim 2, wherein the solid form exhibits an X-ray powder diffraction reflection at a 2-theta value of 11.1°±0.3 and 21.2°±0.3.

4. The solid form of claim 2, wherein the solid form exhibits an X-ray powder diffraction reflection at a 2-theta value of 15.8°±0.3 and 22.0°=0.3.

5. The solid form of claim 2, wherein the solid form exhibits an X-ray powder diffraction reflection at a 2-theta value of 13.9°±0.3, 18.5° 0.3, 21.7°±0.3, and 22.5°±0.3.

6. The solid form of claim 2, wherein the solid form exhibits an X-ray powder diffraction reflection at a 2-theta value of 9.7°±0.3, 23.3°±0.3, and 23.8°±0.3.

7. The solid form of claim 1, wherein the solid form exhibits at least one X-ray powder diffraction reflection selected from 9.7°±0.3, 11.1°±0.3, 13.9°±0.3, 15.8°±0.3, 18.5°±0.3, 19.7°±0.3, 21.2°±0.3, 21.7°±0.3, 22.0°±0.3, 22.5°±0.3, 23.3°±0.3, and 23.8°=0.3.

8. The solid form of claim 7, wherein the solid form exhibits at least two X-ray powder diffraction reflections selected from 9.7°±0.3, 11.1°±0.3, 13.9°±0.3, 15.8°±0.3, 18.5°±0.3, 19.7°±0.3, 21.2°±0.3, 21.7°±0.3, 22.0°±0.3, 22.5°±0.3, 23.3°±0.3, and 23.8°±0.3.

9. The solid form of claim 8, wherein the solid form exhibits at least three X-ray powder diffraction reflections selected from 9.7°±0.3, 11.1°±0.3, 13.9°±0.3, 15.8°±0.3, 18.5°±0.3, 19.7°±0.3, 21.2°±0.3, 21.7°±0.3, 22.0°±0.3, 22.5°±0.3, 23.3°±0.3, and 23.8°=0.3.

10. The solid form of claim 9, wherein the solid form exhibits at least four X-ray powder diffraction reflections selected from 9.7°±0.3, 11.1°±0.3, 13.9°±0.3, 15.8°±0.3, 18.5°±0.3, 19.7°±0.3, 21.2°±0.3, 21.7°±0.3, 22.0°±0.3, 22.5°±0.3, 23.3°±0.3, and 23.8°±0.3.

11. The solid form of claim 10, wherein the solid form exhibits at least five X-ray powder diffraction reflections selected from 9.7°±0.3, 11.1°±0.3, 13.9°±0.3, 15.8°±0.3, 18.5°±0.3, 19.7°±0.3, 21.2°±0.3, 21.7°±0.3, 22.0°±0.3, 22.5°±0.3, 23.3°±0.3, and 23.8°±0.3.

12. The solid form of claim 11, wherein the solid form exhibits at least six X-ray powder diffraction reflections selected from 9.7°±0.3, 11.1°±0.3, 13.9°±0.3, 15.8°±0.3, 18.5°±0.3, 19.7°±0.3, 21.2°=0.3, 21.7°±0.3, 22.0°±0.3, 22.5°±0.3, 23.3°±0.3, and 23.8°±0.3.

13. The solid form of claim 1, wherein the solid form exhibits an X-ray powder diffraction reflection at a 2-theta value of the crystalline solid state form of Compound 2 exhibits at least one X-ray powder diffraction reflection selected from 20.3°±0.2, 23.4°±0.2, and 24.0°±0.2.

14. The solid form of claim 1, wherein the solid form exhibits the X-ray powder diffraction pattern as shown in FIG. 3.

15. The solid form of claim 1, wherein the solid form exhibits a differential scanning calorimetry thermogram comprising an endothermic peak at 229.9° C.±5.0.

16. The solid form of claim 1, wherein the solid form exhibits the differential scanning calorimetry thermogram as shown in FIG. 4.

17. The solid form of claim 1, wherein the solid form exhibits less than 1.0%±0.5 weight loss up to 160° C.±10.0 as determined by thermogravimetric analysis.

18. The solid form of claim 1, wherein the solid form exhibits the thermogravimetric analysis thermogram as shown in FIG. 4.

19. A pharmaceutical composition comprising the solid form of claim 1 and a pharmaceutically acceptable excipient.

20. The pharmaceutical composition of claim 19, further comprising a disintegrating agent.

21. The pharmaceutical composition of claim 20, wherein the disintegrating agent is croscarmellose sodium.

22. A method of inhibiting receptor tyrosine kinase effector RAF comprising administering to the subject with a condition in need thereof, the solid form of claim 1.

23. The method of claim 22, wherein the condition is cancer or neoplastic disease.

* * * * *